US008415456B2

(12) United States Patent
Nellis et al.

(10) Patent No.: US 8,415,456 B2
(45) Date of Patent: Apr. 9, 2013

(54) SUBSTITUTED IL-15 POLYPEPTIDES

(75) Inventors: David F. Nellis, Frederick, MD (US); Dennis F. Michiel, Hagerstown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 26 days.

(21) Appl. No.: 12/915,363

(22) Filed: Oct. 29, 2010

(65) Prior Publication Data

US 2011/0059042 A1 Mar. 10, 2011

Related U.S. Application Data

(63) Continuation-in-part of application No. PCT/US2009/042355, filed on Apr. 30, 2009.

(60) Provisional application No. 61/049,165, filed on Apr. 30, 2008.

(51) Int. Cl.
*C07K 14/54* (2006.01)
*A61K 38/20* (2006.01)
*A61K 45/00* (2006.01)

(52) U.S. Cl. ........................ 530/351; 514/1.1; 424/85.2

(58) Field of Classification Search ........................ None
See application file for complete search history.

(56) References Cited

U.S. PATENT DOCUMENTS

| | | | | |
|---|---|---|---|---|
| 5,747,024 | A | 5/1998 | Grabstein et al. | |
| 7,008,624 | B1 | 3/2006 | Grabstein et al. | |
| 2005/0171339 | A1* | 8/2005 | Sugo et al. | 530/388.15 |

FOREIGN PATENT DOCUMENTS

| | | | |
|---|---|---|---|
| WO | WO 95/27722 | A1 | 10/1995 |
| WO | WO 96/372231 | A1 | 11/1996 |
| WO | WO 2004/058278 | A1 | 7/2004 |
| WO | WO 2007/084342 | | 7/2007 |

OTHER PUBLICATIONS

GenBank Accession No. CAA71044.1, May 1997.*
Carvalho et al., "Deamidations in recombinant human phenylalanine hydroxylase. Identification of labile asparagine residues and functional characterization of Asn → Asp mutant forms," *J. Biol. Chem.*, 278 (17), 15142-15152 (2003).
Chen et al., "Substitution of asparagine residues in *Aspergillus awamori* glucoamylase by site-directed mutagenesis to eliminate N-glycosylation and inactivation by deamidation," *Biochem. J.*, 301, 275-281 (1994).
Daumy et al., "Reduction of biological activity of murine recombinant interleukin-1β by selective deamidation at asparagine-149," *FEBS Lett.*, 278 (1), 98-102 (1991).
Diab et al., "IL-15: targeting $CD8^+$ T cells for immunotherapy," *Cytotherapy*, 7 (1), 23-35 (2005).
Di Salvo et al., "Deamidation of asparagine residues in a recombinant serine hydroxymethyltransferase[1]," *Arch. Biochem. Biophys.*, 372 (2), 271-279 (1999).
Hsu et al., "Selective deamidation of recombinant human stem cell factor during in vitro aging: isolation and characterization of the aspartyl and isoaspartyl homodimers and heterodimers," *Biochemistry*, 37 (8), 2251-2262 (1998).
Robinson et al., "Molecular Clocks: Deamidation of Asparaginyl and Glutaminyl Residues in Peptides and Proteins," Althouse Press, Cave Junction, OR, pp. 82-83 (available at http://book.deamidation.org/MolecularClocks.pdf) (2004).
Rodrigues et al., "Role of IL-15 and IL-21 in viral immunity: applications for vaccines and therapies," *Expert Rev. Vaccines*, 8 (2), 167-177 (2009).
Sasaoki et al., "Deamidation at asparagine-88 in recombinant human interleukin 2," *Chem. Pharm. Bull.* (Tokyo), 40 (4), 976-980 (1992).
Wingfield et al., "Recombinant-derived interleukin-1α stabilized against specific deamidation," *Protein Eng.*, 1 (5), 413-417 (1987).
Zhang et al., "Characterization of asparagine deamidation and aspartate isomerization in recombinant human interleukin-11," *Pharm. Res.*, 19 (8), 1223-1231 (2002).

* cited by examiner

*Primary Examiner* — Robert Landsman
*Assistant Examiner* — Bruce D Hissong
(74) *Attorney, Agent, or Firm* — Leydig, Voit & Mayer

(57) ABSTRACT

The invention provides IL-15 amino acid sequences with amino acid substitutions that reduce or eliminate deamidation of IL-15 and degradation by-products. The invention also provides DNA sequences that encode the substituted amino acid sequences, a pharmaceutical composition comprising the substituted IL-15 amino acid sequence and a pharmaceutically acceptable carrier, and a method of treating a condition in a mammalian host comprising administering to the host the substituted IL-15 amino acid sequence or the pharmaceutical composition including the substituted IL-15 amino acid sequence in an amount effective to treat the condition in the host.

18 Claims, 17 Drawing Sheets

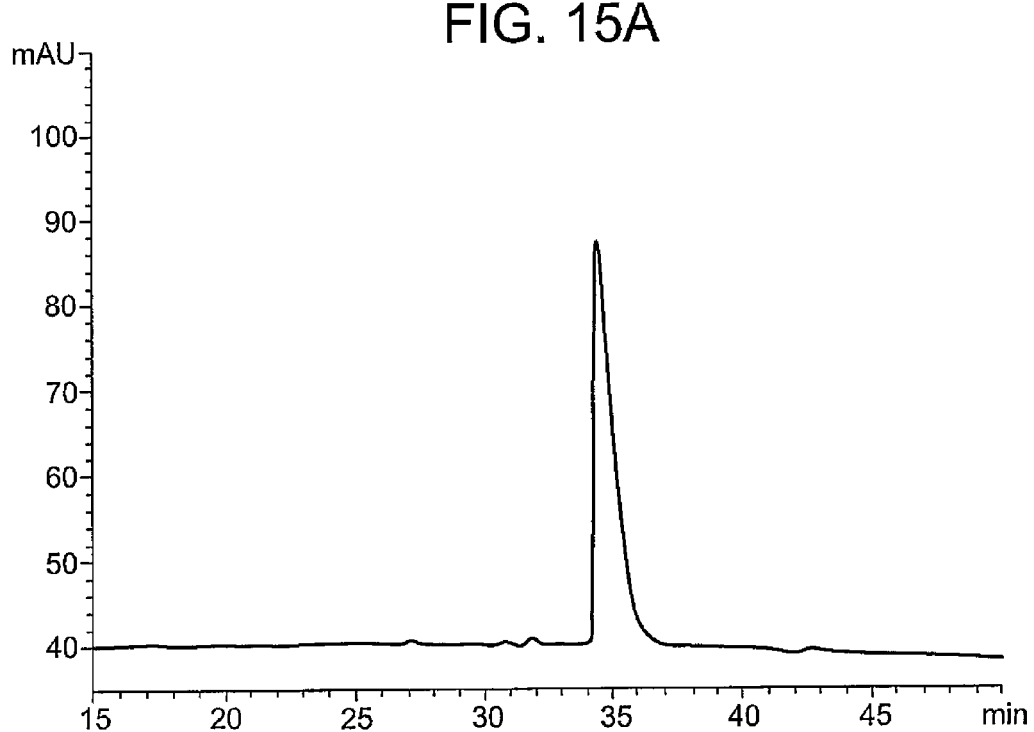
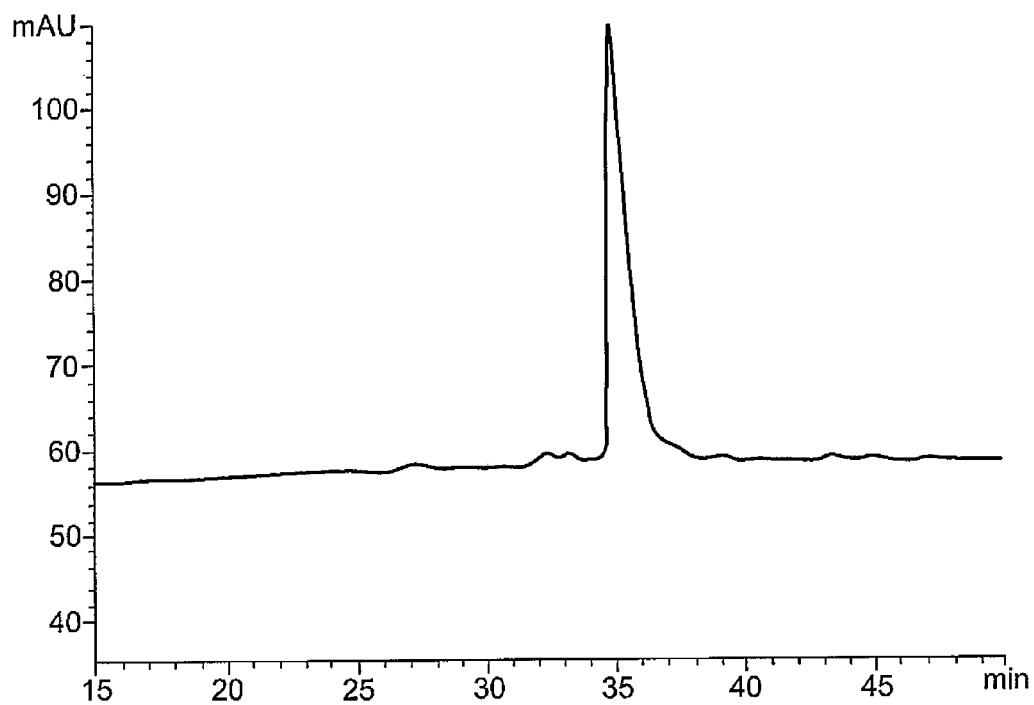

SEQUENCE LISTING

```
<160> NUMBER OF SEQ ID NOS: 25

<210> SEQ ID NO 1
<211> LENGTH: 114
<212> TYPE: PRT
<213> ORGANISM: Artificial Sequence
<220> FEATURE:
<223> OTHER INFORMATION: Substituted human IL-15 segment
<220> FEATURE:
<221> NAME/KEY: misc_feature
<222> LOCATION: (71)..(72)
<223> OTHER INFORMATION: Xaa is Ser, Ala or Asn
<220> FEATURE:
<221> NAME/KEY: misc_feature
<222> LOCATION: (77)..(77)
<223> OTHER INFORMATION: Xaa is Gln, Ser, Lys, Ala, or Glu
<220> FEATURE:
<221> NAME/KEY: misc_feature
<222> LOCATION: (78)..(78)
<223> OTHER INFORMATION: Xaa is ser, Ala, or Gly

<400> SEQUENCE: 1

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Xaa Xaa Ser Leu Ser Ser Xaa Xaa Asn Val
 65                 70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 341
<212> TYPE: DNA
<213> ORGANISM: Artificial Sequence
<220> FEATURE:
<223> OTHER INFORMATION: Substituted human IL-15 segment
<220> FEATURE:
<221> NAME/KEY: misc_feature
<222> LOCATION: (211)..(213)
<223> OTHER INFORMATION: nnn is aac, aat, agt, agc, tca, tcc, tcg, tct,
      gct, gca, gcc, gcg
<220> FEATURE:
<221> NAME/KEY: misc_feature
<222> LOCATION: (214)..(216)
<223> OTHER INFORMATION: nnn is aac, aat, agt, agc, tca, tcc, tcg, tct,
      gct, gca, gcc, gcg
<220> FEATURE:
<221> NAME/KEY: misc_feature
<222> LOCATION: (229)..(231)
<223> OTHER INFORMATION: nnn is caa, cag, agt, agc, tca, tcc, tcg, tct,
      gct, gca, gcc, gcg, gag, gaa, aaa, aag
```

<220> FEATURE:
<221> NAME/KEY: misc_feature
<222> LOCATION: (232)..(234)
<223> OTHER INFORMATION: nnn is gga, ggc, ggg, ggt, gct, gca, gcc, gcg,
      agt, agc, tca, tcc, tcg, tct

<400> SEQUENCE: 2

```
aactgggtga atgtaataag tgatttgaaa aaaattgaag atcttattca atctatgcat      60
attgatgcta ctttatatac ggaaagtgat gttcaccccca gttgcaaagt aacagcaatg   120
aagtgctttc tcttggagtt acaagttatt tcacttgagt ccggagatgc aagtattcat   180
gatacagtag aaaatctgat catcctagca nnnnnnagtt tgtcttctnn nnnnaatgta   240
acagaatctg gatgcaaaga atgtgaggaa ctggaggaaa aaaatattaa agaattttg    300 cagagttttg tacatattgt ccaaatgttc atcaacactt c                       341
```

<210> SEQ ID NO 3
<211> LENGTH: 114
<212> TYPE: PRT
<213> ORGANISM: Artificial Sequence
<220> FEATURE:
<223> OTHER INFORMATION: Substituted human IL-15 segment
<220> FEATURE:
<221> NAME/KEY: misc_feature
<222> LOCATION: (71)..(72)
<223> OTHER INFORMATION: Xaa is Ser, Ala or Asn
<220> FEATURE:
<221> NAME/KEY: misc_feature
<222> LOCATION: (77)..(77)
<223> OTHER INFORMATION: Xaa is Gln, Ser, Lys, Ala, Glu, or Asn
<220> FEATURE:
<221> NAME/KEY: misc_feature
<222> LOCATION: (78)..(78)
<223> OTHER INFORMATION: Xaa is Ser or Ala

<400> SEQUENCE: 3

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Xaa Xaa Ser Leu Ser Ser Xaa Xaa Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 4
<211> LENGTH: 341
<212> TYPE: DNA
<213> ORGANISM: Artificial Sequence
<220> FEATURE:
<223> OTHER INFORMATION: Substituted human IL-15 segment
<220> FEATURE:
<221> NAME/KEY: misc_feature
<222> LOCATION: (211)..(213)
<223> OTHER INFORMATION: nnn is aac, aat, agt, agc, tca, tcc, tcg, tct,
      gct, gca, gcc, gcg
<220> FEATURE:
<221> NAME/KEY: misc_feature
<222> LOCATION: (214)..(216)

<223> OTHER INFORMATION: nnn is aac, aat, agt, agc, tca, tcc, tcg, tct,
      gct, gca, gcc, gcg
<220> FEATURE:
<221> NAME/KEY: misc_feature
<222> LOCATION: (229)..(231)
<223> OTHER INFORMATION: nnn is caa, cag, agt, agc, tca, tcc, tcg, tct,
      gct, gca, gcc, gcg, gag, gaa, aaa, aag, aac or aat
<220> FEATURE:
<221> NAME/KEY: misc_feature
<222> LOCATION: (232)..(234)
<223> OTHER INFORMATION: nnn is gct, gca, gcc, gcg, agt, agc, tca, tcc,
      tcg, or tct

<400> SEQUENCE: 4

```
aactgggtga atgtaataag tgatttgaaa aaaattgaag atcttattca atctatgcat    60
attgatgcta ctttatatac ggaaagtgat gttcacccca gttgcaaagt aacagcaatg   120
aagtgctttc tcttggagtt acaagttatt tcacttgagt ccggagatgc aagtattcat   180
gatacagtag aaaatctgat catcctagca nnnnnnagtt tgtcttctnn nnnnaatgta   240
acagaatctg gatgcaaaga atgtgaggaa ctggaggaaa aaaatattaa agaattttg    300
cagagttttg tacatattgt ccaaatgttc atcaacactt c                      341
```

<210> SEQ ID NO 5
<211> LENGTH: 48
<212> TYPE: PRT
<213> ORGANISM: Artificial Sequence
<220> FEATURE:
<223> OTHER INFORMATION: Natural leader sequence for human IL-15

<400> SEQUENCE: 5

```
Met Arg Ile Ser Lys Pro His Leu Arg Ser Ile Ser Ile Gln Cys Tyr
1               5                   10                  15
Leu Cys Leu Leu Leu Asn Ser His Phe Leu Thr Glu Ala Gly Ile His
            20                  25                  30
Val Phe Ile Leu Gly Cys Phe Ser Ala Gly Leu Pro Lys Thr Glu Ala
        35                  40                  45
```

<210> SEQ ID NO 6
<211> LENGTH: 144
<212> TYPE: DNA
<213> ORGANISM: Artificial Sequence
<220> FEATURE:
<223> OTHER INFORMATION: Natural leader sequence of human IL-15

<400> SEQUENCE: 6

```
atgagaattt cgaaaccaca tttgagaagt atttccatcc agtgctactt gtgtttactt    60
ctaaacagtc attttctaac tgaagctggc attcatgtct cattttggg ctgtttcagt    120
gcagggcttc ctaaaacaga agcc                                          144
```

<210> SEQ ID NO 7
<211> LENGTH: 114
<212> TYPE: PRT
<213> ORGANISM: Artificial Sequence
<220> FEATURE:
<223> OTHER INFORMATION: Unsubstituted human IL-15 segment

<400> SEQUENCE: 7

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
```

Val Ile Ser Leu Glu Ser Gly Asp Ala Ser Ile His Asp Thr Val Glu
                50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 8
<211> LENGTH: 341
<212> TYPE: DNA
<213> ORGANISM: Artificial Sequence
<220> FEATURE:
<223> OTHER INFORMATION: Unsubstituted human IL-15 DNA sequence segment

<400> SEQUENCE: 8
aactgggtga atgtaataag tgatttgaaa aaaattgaag atcttattca atctatgcat      60
attgatgcta ctttatatac ggaaagtgat gttcacccca gttgcaaagt aacagcaatg     120
aagtgctttc tcttggagtt acaagttatt tcacttgagt ccggagatgc aagtattcat     180
gatacagtag aaaatctgat catcctagca acaacagtt tgtcttctaa tgggaatgta      240
acagaatctg gatgcaaaga atgtgaggaa ctggaggaaa aaaatattaa agaatttttg     300
cagagttttg tacatattgt ccaaatgttc atcaacactt c                         341

<210> SEQ ID NO 9
<211> LENGTH: 51
<212> TYPE: DNA
<213> ORGANISM: Artificial Sequence
<220> FEATURE:
<223> OTHER INFORMATION: Primer

<400> SEQUENCE: 9
ctgatcatcc tagcaaacaa cagtttgtct tctcagggga atgtaacaga a                51

<210> SEQ ID NO 10
<211> LENGTH: 51
<212> TYPE: DNA
<213> ORGANISM: Artificial Sequence
<220> FEATURE:
<223> OTHER INFORMATION: Primer

<400> SEQUENCE: 10
ctgatcatcc tagcaaacaa cagtttgtct tctagtggga atgtaacaga a                51

<210> SEQ ID NO 11
<211> LENGTH: 51
<212> TYPE: DNA
<213> ORGANISM: Artificial Sequence
<220> FEATURE:
<223> OTHER INFORMATION: Primer

<400> SEQUENCE: 11
ctgatcatcc tagcaaacaa cagtttgtct tctgctggga atgtaacaga a                51

<210> SEQ ID NO 12
<211> LENGTH: 51
<212> TYPE: DNA
<213> ORGANISM: Artificial Sequence
<220> FEATURE:
<223> OTHER INFORMATION: Primer

```
<400> SEQUENCE: 12
ctgatcatcc tagcaagcag cagtttgtct tctagtggga atgtaacaga a        51

<210> SEQ ID NO 13
<211> LENGTH: 51
<212> TYPE: DNA
<213> ORGANISM: Artificial Sequence
<220> FEATURE:
<223> OTHER INFORMATION: Primer

<400> SEQUENCE: 13
ctgatcatcc tagcaaacaa cagtttgtct tctaatgcga atgtaacaga a        51

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
ctgatcatcc tagcaaacaa cagtttgtct tctaatagca atgtaacaga a        51

<210> SEQ ID NO 15
<211> LENGTH: 51
<212> TYPE: DNA
<213> ORGANISM: Artificial Sequence
<220> FEATURE:
<223> OTHER INFORMATION: Primer

<400> SEQUENCE: 15
ctgatcatcc tagcaaacaa cagtttgtct tctgagggga atgtaacaga a        51

<210> SEQ ID NO 16
<211> LENGTH: 52
<212> TYPE: DNA
<213> ORGANISM: Artificial Sequence
<220> FEATURE:
<223> OTHER INFORMATION: Synthetic

<400> SEQUENCE: 16
cctagcaaac aacagtttgt cttctgctgg gaatgtaaca gaatctggat gc       52

<210> SEQ ID NO 17
<211> LENGTH: 52
<212> TYPE: DNA
<213> ORGANISM: Artificial Sequence
<220> FEATURE:
<223> OTHER INFORMATION: Synthetic

<400> SEQUENCE: 17
gcatccagat tctgttacat tcccagcaga agacaaactg ttgtttgcta gg       52

<210> SEQ ID NO 18
<211> LENGTH: 52
<212> TYPE: DNA
<213> ORGANISM: Artificial Sequence
<220> FEATURE:
<223> OTHER INFORMATION: Synthetic

<400> SEQUENCE: 18
cctagcaaac aacagtttgt cttctagtgg gaatgtaaca gaatctggat gc       52

<210> SEQ ID NO 19
<211> LENGTH: 52
```

<212> TYPE: DNA
<213> ORGANISM: Artificial Sequence
<220> FEATURE:
<223> OTHER INFORMATION: Synthetic

<400> SEQUENCE: 19
gcatccagat tctgttacat tcccactaga agacaaactg ttgtttgcta gg    52

<210> SEQ ID NO 20
<211> LENGTH: 52
<212> TYPE: DNA
<213> ORGANISM: Artificial Sequence
<220> FEATURE:
<223> OTHER INFORMATION: Synthetic

<400> SEQUENCE: 20
cctagcaaac aacagtttgt cttctcaagg gaatgtaaca gaatctggat gc    52

<210> SEQ ID NO 21
<211> LENGTH: 52
<212> TYPE: DNA
<213> ORGANISM: Artificial Sequence
<220> FEATURE:
<223> OTHER INFORMATION: Synthetic

<400> SEQUENCE: 21
gcatccagat tctgttacat tcccttgaga agacaaactg ttgtttgcta gg    52

<210> SEQ ID NO 22
<211> LENGTH: 52
<212> TYPE: DNA
<213> ORGANISM: Artificial Sequence
<220> FEATURE:
<223> OTHER INFORMATION: Synthetic

<400> SEQUENCE: 22
cctagcaaac aacagtttgt cttctaatgc gaatgtaaca gaatctggat gc    52

<210> SEQ ID NO 23
<211> LENGTH: 52
<212> TYPE: DNA
<213> ORGANISM: Artificial Sequence
<220> FEATURE:
<223> OTHER INFORMATION: Synthetic

<400> SEQUENCE: 23
gcatccagat tctgttacat tcgcattaga agacaaactg ttgtttgcta gg    52

<210> SEQ ID NO 24
<211> LENGTH: 71
<212> TYPE: DNA
<213> ORGANISM: Artificial Sequence
<220> FEATURE:
<223> OTHER INFORMATION: Synthetic

<400> SEQUENCE: 24
cagtagaaaa tctgatcatc ctagcaagcg ccagtttgtc ttctgctggg aatgtaacag    60
aatctggatg c    71

<210> SEQ ID NO 25
<211> LENGTH: 71
<212> TYPE: DNA
<213> ORGANISM: Artificial Sequence
<220> FEATURE:
<223> OTHER INFORMATION: Synthetic

<400> SEQUENCE: 25

```
gcatccagat tctgttacat tcccagcaga agacaaactg gcgcttgcta ggatgatcag      60
attttctact g                                                          71
```

SUBSTITUTED IL-15 POLYPEPTIDES

CROSS-REFERENCE TO RELATED APPLICATIONS

This patent application is a continuation-in-part of International Patent Application No. PCT/US2009/042355, filed on Apr. 30, 2009, which claims the benefit of U.S. Provisional Patent Application No. 61/049,165, filed Apr. 30, 2008, each of which is incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 9,130 Byte ASCII (Text) file named "706942ST25.TXT," created on Sep. 17, 2010.

BACKGROUND OF THE INVENTION

Interleukin-15 (IL-15) is a vertebrate immune system modulating protein (cytokine) that stimulates the proliferation and differentiation of T-cells. In the clinical context, IL-15 is useful for the treatment of any of a variety of conditions such as, e.g., cancer. The ex-vivo manufacture of IL-15, however, can be problematic, and there is a need in the art for improved IL-15 products.

BRIEF SUMMARY OF THE INVENTION

The invention provides substituted IL-15 amino acid sequences that reduce or eliminate deamidation, and the invention also provides substituted gene sequences that encode the substituted IL-15 amino acid sequences. The substituted IL-15 amino acid sequences advantageously facilitate the refolding, purification, storage, characterization, and clinical testing of IL-15.

In one embodiment, the invention provides an amino acid sequence comprising SEQ ID NO:1 or SEQ ID NO:3.

In another embodiment, the invention provides a nucleic acid sequence comprising SEQ ID NO:2 or SEQ ID NO:4.

A pharmaceutical composition according to another embodiment of the invention comprises SEQ ID NO:1 or SEQ ID NO:3.

Additionally, an embodiment of the invention provides a method of treating a condition in a mammalian host, comprising administering to the host an amino acid sequence comprising SEQ ID NO:1 or SEQ ID NO:3.

Isolated cells and expression vectors comprising SEQ ID NO:2 or SEQ ID NO:4 are also provided according to an embodiment of the invention.

BRIEF DESCRIPTION OF THE SEVERAL VIEWS OF THE DRAWINGS

FIG. 15A shows a chromatogram from an RP-HPLC analysis of N71S/N72A/N77A substituted IL-15 prior to incubation at 37° C. for one week.

FIG. 15B shows a chromatogram from an RP-HPLC analysis of N71S/N72A/N77A substituted IL-15 following incubation at 37° C. for one week.

DETAILED DESCRIPTION OF THE INVENTION

Figure 1:
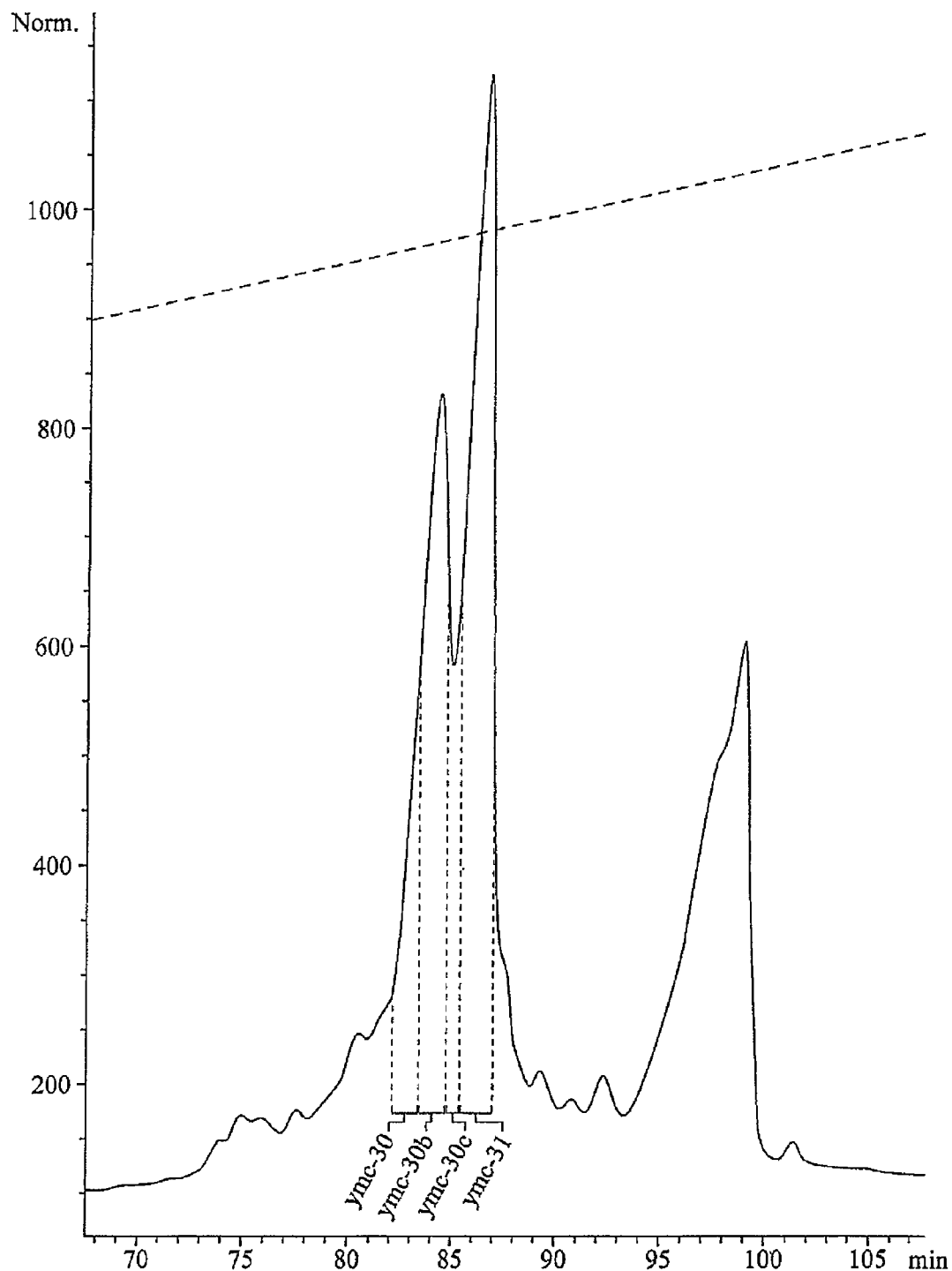
FIG. 1 shows a chromatogram from a Reverse Phase High Performance Liquid Chromatography (RP-HPLC) separation of an unsubstituted IL-15 preparation after partial purification by preparative hydrophobic interaction chromatography (HIC Tail Pool) (YMC-C4 column, 4.6 mm×150 mm, 5-μm beads, 20° C. column temperature, at 0.9 mL/minute flow rate, load at 0% ethanol, elution by 42-77% linear gradient of ethanol in water with 20 mM ammonium acetate: acetate, 0.2 mM $CaCl_2$ buffer, pH approximately 5, conducted over 21 column volumes).

The invention provides substituted IL-15 amino acid sequences that reduce or eliminate deamidation, and also provides substituted gene sequences that encode the substituted IL-15 amino acid sequences. The substituted IL-15 amino acid sequences advantageously facilitate the refolding, purification, storage, characterization, and clinical testing of IL-15. For example, the IL-15 products according to the invention may have a chromatographic profile that shows a reduced presence of degradation by-products.

In particular, one embodiment of the invention provides an amino acid sequence comprising SEQ ID NO:1, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, and Glu; and Xaa78 is selected from the group consisting of Ser, Ala, and Gly.

Another embodiment of the invention provides an amino acid sequence comprising SEQ ID NO:3, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, Glu, and Asn; and Xaa78 is selected from the group consisting of Ser and Ala.

Still another embodiment of the invention provides a pharmaceutical composition comprising SEQ ID NO:1, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, and Glu; and Xaa78 is selected from the group consisting of Ser, Ala, and Gly.

Another embodiment of the invention provides a pharmaceutical composition comprising SEQ ID NO:3, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, Glu, and Asn; and Xaa78 is selected from the group consisting of Ser and Ala.

Another embodiment of the invention provides a method of treating a condition in a mammalian host, comprising administering to the host an amino acid sequence comprising SEQ ID NO:1 or a pharmaceutical composition comprising SEQ ID NO:1, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, and Glu; and Xaa78 is selected from the group consisting of Ser, Ala, and Gly.

Another embodiment of the invention provides a method of treating a condition in a mammalian host, comprising administering to the host an amino acid sequence comprising SEQ ID NO:3 or a pharmaceutical composition comprising SEQ ID NO:3, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, Glu, and Asn; and Xaa78 is selected from the group consisting of Ser and Ala.

Still another embodiment of the invention provides an isolated or purified amino acid sequence comprising SEQ ID NO:1, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, and Glu; and Xaa78 is selected from the group consisting of Ser, Ala, and Gly.

Another embodiment of the invention provides an isolated or purified amino acid sequence comprising SEQ ID NO:3, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, Glu, and Asn; and Xaa78 is selected from the group consisting of Ser and Ala.

Another embodiment of the invention provides a nucleic acid sequence comprising SEQ ID NO:2, wherein NNN at base pairs 229 to 231 is a codon that encodes for an amino acid selected from the group consisting of Gln, Ser, Ala, Lys, and Glu; NNN at base pairs 232 to 234 is a codon that encodes for an amino acid selected from the group consisting of Ser, Ala, or Gly; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides a nucleic acid sequence comprising SEQ ID NO:4, wherein NNN at base pairs 229 to 231 is a codon that encodes for an amino acid selected from the group consisting of Gln, Ser, Ala, Lys, Glu, and Asn; NNN at base pairs 232 to 234 is a codon that encodes for an amino acid selected from the group consisting of Ser or Ala; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides an isolated or purified nucleic acid sequence comprising SEQ ID NO:2, wherein NNN at base pairs 229 to 231 is a codon that encodes for an amino acid selected from the group consisting of Gln, Ser, Ala, Lys, and Glu; NNN at base pairs 232 to 234 is a codon that encodes for an amino acid selected from the group consisting of Ser, Ala, or Gly; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides an isolated or purified nucleic acid sequence comprising SEQ ID NO:4, wherein NNN at base pairs 229 to 231 is a codon that encodes for an amino acid selected from the group consisting of Gln, Ser, Ala, Lys, Glu, and Asn; NNN at base pairs 232 to 234 is a codon that encodes for an amino acid selected from the group consisting of Ser or Ala; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides an isolated cell comprising SEQ ID NO:2, wherein NNN at base pairs 229 to 231 is a codon that encodes for an amino acid selected from the group consisting of Gln, Ser, Ala, Lys, and Glu; NNN at base pairs 232 to 234 is a codon that encodes for an amino acid selected from the group consisting of Ser, Ala, or Gly; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides an isolated cell comprising SEQ ID NO:4, wherein NNN at base pairs 229 to 231 is a codon that encodes for an amino acid selected from the group consisting of Gln, Ser, Ala, Lys, Glu, and Asn; NNN at base pairs 232 to 234 is a codon that encodes for an amino acid selected from the group consisting of Ser or Ala; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Another embodiment of the invention provides an expression vector comprising SEQ ID NO:2, wherein NNN at base pairs 229 to 231 is a codon that encodes for an amino acid selected from the group consisting of Gln, Ser, Ala, Lys, and Glu; NNN at base pairs 232 to 234 is a codon that encodes for an amino acid selected from the group consisting of Ser, Ala, or Gly; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

Still another embodiment of the invention provides an expression vector comprising SEQ ID NO:4, wherein NNN at base pairs 229 to 231 is a codon that encodes for an amino acid selected from the group consisting of Gln, Ser, Ala, Lys, Glu, and Asn; NNN at base pairs 232 to 234 is a codon that encodes for an amino acid selected from the group consisting of Ser or Ala; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn.

The nucleic acids of the invention may, advantageously, be transformed into a host cell, such as a bacterial cell, to produce the amino acid sequences of the invention.

Deamidation of IL-15

The inventors have discovered that deamidation of unsubstituted IL-15 (SEQ ID NO:7) can form degradation by-products of IL-15 when unsubstituted IL-15 is manufactured in vitro. In particular, the inventors have found that deamidation of Asn71, Asn72, and/or Asn77 of SEQ ID NO:7 may lead to degradation by-products that may reduce the purity of the yield of the manufactured IL-15.

It is believed by the inventors that when IL-15 is expressed in mammalian cells, asparagine residues can be protected from deamidation by natural glycosylation that shields the asparagines from deamidation or by rapid, native refolding into conformations less susceptible to asparagine side-chain attack. However, it appears that when IL-15 is expressed in bacterial systems and isolated by solubilizing the inclusion body in, e.g., guanidinium hydrochloride or urea, native glycosylation and refolding may not occur to protect the asparagines from deamidation. Accordingly, solubilized, in vitro-produced IL-15 may be susceptible to deamidation.

The inventors believe that Asn77 of SEQ ID NO:7 may be most susceptible to deamidation, and Asn71 and Asn72 may also be susceptible to deamidation, based on the relative deamidation rates of the Asn residues. Deamidation rates may be estimated and expressed as half time ($t\frac{1}{2}$) in days. For example, Robinson, N. E. and Robinson, A. B. (2004) *Molecular Clocks Deamidation of Asparaginyl and Glutaminyl Residues in Peptides and Proteins*, Althouse Press, Cave Junction, Oreg., sets forth first-order deamidation half-times of various pentapeptides with the formula GlyXxxAsnYyyGly at pH 7.4, 37° C., 0.15 M Tris HCl (e.g., Table 6-2 of Robinson et al.). Under these conditions, Asn77 of SEQ ID NO:7 may have a half time of less than approximately 1 day (0.96 VA). The Asn77 of SEQ ID NO:7 may, therefore, be susceptible to deamidation. Under these conditions, Asn71 and Asn72 of SEQ ID NO:1 may have a half time of approximately 20 VA and approximately 15.4 $t\frac{1}{2}$, respectively. Asn71 and Asn72 of SEQ ID NO:7 may, therefore, also be susceptible to deamidation, but to a lesser degree than Asn77.

Without being bound to a particular theory, it is believed that in the deamidation of unsubstituted IL-15 (SEQ ID NO:7), the asparagine side chain attacks the C-side peptide backbone nitrogen of the Asn residue. It is believed that this attack forms a cyclic succinimide intermediate that may racimize and linearize to form four degradation products of IL-15, i.e., D-isoaspartic acid, L-isoaspartic acid, D-aspartic acid, and L-aspartic acid. Deamidation results in the replacement of the amide group of asparagine with the carboxylic acid side chain of aspartic acid. The carboxylic acid side chain of either aspartic acid or isoaspartic acid is more negatively charged, less hydrophobic, and more polar than the neutral asparagine amide group.

The degradation by-products formed by the deamidation of IL-15 may be, therefore, heterogeneous in terms of charge, polarity, and hydrophobicity. These degradation by-products of IL-15 complicate manufacture and characterization of the IL-15 (SEQ ID NO:7) product, and may lead to the presence of impurities such as host cell proteins, mis-folded proteins or aggregates in an IL-15 preparation. In addition, preparations including deamidated IL-15 have undesirably complex chromatographic elution profiles including, e.g., broad and split peaks. For example, in HPLC analyses of unsubstituted IL-15, the deamidation of IL-15 may be observed as a close-doublet heterogeneity (at high pH, e.g., approximately 5.0 or higher) or as a triplet heterogeneity (at low pH, e.g., approximately 2.0 or lower). These deamidation by-products may be found in approximately 30 to 80% of refolded IL-15 molecules.

Amino Acid Substitutions

The invention provides substituted IL-15 amino acid sequences, and also provides substituted gene sequences that encode the substituted IL-15 amino acid sequences. In general, the substituted amino acid sequences SEQ ID NO:1 and SEQ ID NO:3 correspond with the native, unsubstituted IL-15 SEQ ID NO:7 with SEQ ID NO:1 and SEQ ID NO:3 having at least one substitution when compared to SEQ ID NO:7. Preferably, one or both of the native Asn77 and Gly78 of SEQ ID NO:7 is substituted, and either or both of the native Asn71 and Asn72 of SEQ ID NO:7 may be substituted or may be unsubstituted.

In particular, the invention provides an amino acid sequence comprising SEQ ID NO:1, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, and Glu; and Xaa78 is selected from the group consisting of Ser, Ala, and Gly. SEQ ID NO:1 generally corresponds to the native, unsubstituted IL-15 amino acid sequence SEQ ID NO:7 with the exception that in SEQ ID NO:1, at least Asn77 is substituted, and Gly78, Asn71, and Asn72 substituted or unsubstituted.

The amino acid sequence comprising SEQ ID NO:1 may be generated from, for example, nucleic acid sequences comprising SEQ ID NO:2, wherein NNN at base pairs 229 to 231 is a codon that encodes for an amino acid selected from the group consisting of Gln, Ser, Ala, Lys, and Glu; NNN at base pairs 232 to 234 is a codon that encodes for an amino acid selected from the group consisting of Ser, Ala, or Gly; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn, as set forth, for example, in Table 2 below. SEQ ID NO:2 generally corresponds to the native, unsubstituted IL-15 nucleic acid sequence SEQ ID NO:8 with the exception that in SEQ ID NO:2, at least NNN at base pairs 229 to 231 is substituted, and NNN at base pairs 232 to 234, NNN at base pairs 211 to 213, and NNN at base pairs 214 to 216 may be substituted or unsubstituted.

The invention also provides an amino acid sequence comprising SEQ ID NO:3, wherein Xaa71 is selected from the group consisting of Ser, Ala and Asn; Xaa72 is selected from the group consisting of Ser, Ala and Asn; Xaa77 is selected from the group consisting of Gln, Ser, Lys, Ala, Glu, and Asn; and Xaa78 is selected from the group consisting of Ser and Ala. SEQ ID NO:3 generally corresponds to the native, unsubstituted IL-15 amino acid sequence SEQ ID NO:7 with the exception that in SEQ ID NO:3, at least Gly78 is substituted, and Asn77, Asn71, and Asn72 may be substituted or unsubstituted.

The amino acid sequence comprising SEQ ID NO:3 may be generated from nucleic acid sequences comprising SEQ ID NO:4, wherein NNN at base pairs 229 to 231 is a codon that encodes for an amino acid selected from the group consisting of Gln, Ser, Ala, Lys, Glu, and Asn; NNN at base pairs 232 to 234 is a codon that encodes for an amino acid selected from the group consisting of Ser or Ala; NNN at base pairs 211 to 213 is a codon that encodes for an amino acid selected from the group consisting of Ser, Ala and Asn; and NNN at base pairs 214 to 216 is a codon that encodes for an amino acid selected from the group consisting of Ser, Ala and Asn, as set forth, for example, in Table 2 below. SEQ ID NO:4 generally corresponds to the native, unsubstituted IL-15 nucleic acid sequence SEQ ID NO:8 with the exception that in SEQ ID NO:4, at least NNN at base pairs 232 to 234 is substituted, and NNN at base pairs 229 to 231, NNN at base pairs 211 to 213, and NNN at base pairs 214 to 216 may be substituted or unsubstituted.

In general, genetic substitutions that remove an A/T and insert a C/G may be preferred. Because steric forces may interfere with hybridization of the primer with the template, primers may be more effective when the genetic substitution removes an A/T and replaces it with C/G.

Also, genetic substitutions that require a single point mutation may be preferred over genetic substitutions that require a double or triple point mutation, and genetic substitutions that require a double point mutation may be preferable to genetic substitutions that require a triple point mutation.

Xaa77 Substitutions

In one embodiment, Xaa77 is substituted with Gln, Ser, Lys, Ala, or Glu. Preferably, Xaa77 is Ser or Ala. These substitutions advantageously prevent deamidation of Asn77. Most preferably, Xaa77 is Ser.

TABLE 2

Amino Acids and Corresponding Codons

| Amino Acid | Codon |
|---|---|
| Gln | CAA CAG |
| Ser | AGT AGC TCA TCC TCG TCT |
| Ala | GCT GCA GCC GCG |
| Glu | GAG GAA |
| Lys | AAA AAG |
| Gly | GGA GGC GGG GGT |
| Asn | AAC AAT | a. Xaa77→Gln

Xaa77 of SEQ ID NO:1 and/or SEQ ID NO:3 may be Gln. The substitution of Asn for Gln (Xaa77 is Gln) is advantageously structurally conservative. The Gln substitution (Xaa77 is Gln) adds a methylene group to the side chain while retaining the amide side chain terminus.

The substitutions of Xaa77 with Gln in SEQ ID NO:1 and SEQ ID NO:3 may be generated from nucleic acid SEQ ID NO:2 and SEQ ID NO:4, respectively, in which NNN at base pairs 229 to 231 is any codon that encodes Gln, as shown in Table 2. Preferably, NNN at base pairs 229 to 231 is CAG.

b. Xaa77→Ser

Xaa77 of SEQ ID NO:1 and/or SEQ ID NO:3 may be Ser. The substitution of Asn for Ser (Xaa is Ser) advantageously replaces the uncharged, double h-bond donor with a slightly smaller, uncharged, single h-bond donor. Ser is also, advantageously, minimally immunogenic.

The substitutions of Xaa77 with Ser in SEQ ID NO:1 and SEQ ID NO:3 may be generated from nucleic acid SEQ ID NO:2 and SEQ ID NO:4, respectively, in which NNN at base pairs 229-231 is any codon that encodes Ser, as shown in Table 2. Preferably, NNN at base pairs 229 to 231 is AGT, which requires only a single point mutation.

c. Xaa77→Lys

Alternatively, Xaa77 of SEQ ID NO:1 and/or SEQ ID NO:3 may be Lys. The substitution of Asn for Lys (Xaa77 is Lys) in SEQ ID NO:1 and SEQ ID NO:3 may be generated from nucleic acid SEQ ID NO:2 or SEQ ID NO:4, respectively, in which NNN at base pairs 229-231 is any codon that encodes Lys, as shown in Table 2. For example, NNN at base pairs 229-231 is AAA or AAG, as shown in Table 2.

d. Xaa77→Ala

Alternatively, Xaa77 of SEQ ID NO:1 and/or SEQ ID NO:3 may be Ala. This substitution of Asn for Ala (Xaa77 is Ala) replaces the uncharged, double-h bond donor with a small, uncharged, non-reactive side chain. Ala is also, advantageously, minimally immunogenic.

The substitution of Xaa77 with Ala in SEQ ID NO:1 and SEQ ID NO:3 may be generated from nucleic acid SEQ ID NO:2 and SEQ ID NO:4, respectively, in which NNN at base pairs 229-231 is any codon that encodes Ala, as shown in Table 2. Preferably, NNN at positions 229-231 is GCT.

e. Xaa77→Glu

Alternatively, Xaa77 of SEQ ID NO:1 and/or SEQ ID NO:3 may be Glu. This substitution introduces a negative charge at position 77. Without being bound to a particular theory, it is believed that introducing a negative charge at position 77 may, advantageously, increase IL-15 solubility by increasing same-charge repulsion under physiological conditions.

The substitution of Xaa77 in SEQ ID NO:1 and SEQ ID NO:3 with Glu may be may be generated from nucleic acid SEQ ID NO:2 and SEQ ID NO:4, respectively, in which NNN at base pairs 229-231 is any codon that encodes Glu, as shown in Table 2. Preferably, NNN at base pairs 229-231 is GAG.

Xaa78 Substitutions

Without being bound to a particular theory, it is believed that Gly78 of SEQ ID NO:7 may make the deamidation of Asn77 possible by making the peptide backbone flexible at the site of the side-chain attack of Asn77. Accordingly, the replacement of Xaa78 of SEQ ID NO:1 and/or SEQ ID NO:3 with sterically hindering amino acids Ala or Ser may reduce or eliminate deamidation of Asn77. Ala and Ser are, advantageously, minimally immunogenic and also minimize the alteration of the secondary structure of the protein. Preferably, Xaa78 is Ser.

a. Xaa78→Ala

The substitution of Xaa78 in SEQ ID NO:1 and SEQ ID NO:3 with Ala may be may be generated from nucleic acid SEQ ID NO:2 and SEQ ID NO:4, respectively, in which NNN at base pairs 232-234 is any codon that encodes Ala. For example, the GGG codon at positions 232-234 may be substituted with GCT, GCA, GCC, or GCG, as shown in Table 2. Preferably, NNN at base pairs 232-234 is GCG.

b. Xaa78→Ser

The substitution of Xaa78 with Ser in SEQ ID NO:1 and SEQ ID NO:3 may be generated from nucleic acid SEQ ID NO:2 and SEQ ID NO:4, respectively, in which NNN at base pairs 232-234 is any codon that encodes Ser. For example, NNN at base pairs 232-234 may be AGT, AGC, TCA, TCC, TCG, or TCT, as shown in Table 2. Preferably, NNN at base pairs 232-234 is AGC.

Xaa71 and Xaa72 Substitutions

Optionally, either or both of Xaa71 and Xaa72 of SEQ ID NO:1 and/or SEQ ID NO:3 may be substituted with Ser or Ala. These additional substitutions may, advantageously, also prevent deamidation of Asn71 and Asn72, and may also be particularly advantageous for highly basic or heated solubilization conditions. Preferably, Xaa71 and/or Xaa72 is Ser.

a. Xaa71 and/or Xaa72→Ser

The substitutions of either or both of Xaa71 and Xaa72 with Ser in SEQ ID NO:1 and SEQ ID NO:3 may be generated from nucleic acid SEQ ID NO:2 and SEQ ID NO:4, respectively, in which NNN at base pairs 214-216 and/or 217-219 are/is any codon that encodes Ser. For example, NNN at base pairs 214-216 and/or 217-219 may be AGT, AGC, TCA, TCC, TCG, or TCT, as shown in Table 2. Preferably, NNN at base pairs 214-216 and/or 217-219 are AGC.

b. Xaa71 and/or Xaa72→Ala

The substitutions of either or both of Xaa71 and Xaa72 with Ala in SEQ ID NO:1 and SEQ ID NO:3 may be generated from nucleic acid SEQ ID NO:2 and SEQ ID NO:4, respectively, in which NNN at base pairs 214-216 and/or 217-219 are any codon that encodes Ala. For example, NNN at base pairs 214-216 and/or 217-219 may be GCT, GCA, GCC, or GCG, as shown in Table 2.

Amino acid sequences SEQ ID NO:1 and SEQ ID NO:3 may optionally further include Met or the natural leader sequence SEQ ID NO:5 on the N-terminus. Preferably, SEQ ID NO:1 and SEQ ID NO:3 further include the natural leader sequence SEQ ID NO:5 on the N-terminus when expressed in mammalian cells. Preferably, SEQ ID NO:1 and SEQ ID NO:3 include Met on the N-terminus when expressed in bacterial cells. In an alternative embodiment, the amino acid sequence may consist of SEQ ID NO:1 or SEQ ID NO:3. In still another alternative embodiment, the amino acid sequence may consist of SEQ ID NO:1 or SEQ ID NO:3 with Met or the natural leader sequence SEQ ID NO:5 on the N-terminus.

Nucleic acid sequences SEQ ID NO:2 and SEQ ID NO:4 may optionally further include the start codon ATG or SEQ ID NO:6 encoding the natural leader sequence SEQ ID NO:5 on the 5' end. Preferably, SEQ ID NO:2 and SEQ ID NO:4 further include SEQ ID NO:6 encoding the natural leader sequence SEQ ID NO:5 on the 5' end when expressed in mammalian cells. Preferably, SEQ ID NO:2 and SEQ ID NO:4 include the start codon ATG on the 5' end when expressed in bacterial cells. In an alternative embodiment, the nucleic acid sequence may consist of SEQ ID NO:2 or SEQ ID NO:4. In still another alternative embodiment, the nucleic acid sequence may consist of SEQ ID NO:2 or SEQ ID NO:4 with the start codon ATG or SEQ ID NO:6 encoding the natural leader sequence SEQ ID NO:5 on the 5' end.

The invention also includes variants of the substituted amino acid sequences and nucleic acid sequences that encode variants of the substituted amino acid sequences. The term "variant" as defined herein, includes any peptide which displays the functional aspects of the substituted IL-15 amino acid sequences. Any polypeptide having an amino acid sequence substantially identical to the substituted IL-15 in which one or more residues (other than at least one of the specific amino acid substitutions Xaa77→Gln, Ser, Lys, Ala, or Glu; Xaa78→Scr or Ala; Xaa71→Ser or Ala; or Xaa72→Ser or Ala) have been conservatively substituted with a functionally similar residue and which displays the functional aspects of the substituted IL-15 amino acid sequence is considered to be a "variant."

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For example: 4-hydroxyproline may be substituted for praline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded in the DNA of IL-15.

Techniques for substituting codons in a nucleic acid are well known in the art. The techniques may include, for example, in vitro mutagenesis, PCR, or any other genetic engineering methods known in the art which are suitable for making specific changes to a nucleic acid sequence. Such techniques are described, for example, in *In Vitro Mutagenesis Protocols*, Braman, ed., 2002, Humana Press; in Sankaranarayanan, *Protocols in Mutagenesis*, 2001, Elsevier Science Ltd.; and in Sambrook et al., *Molecular Cloning: A Laboratory Manual*, 3rd ed., Cold Spring Harbor Press, Cold Spring Harbor, N.Y. 2001. Any primers suitable for generating the specific substitutions described herein may be employed. Exemplary primers are set forth in Table 3 below.

TABLE 3

Exemplary Primers

| Amino Acid Substitution | Nucleic Acid Substitution | SEQ ID NO: |
|---|---|---|
| Xaa77→Gln | NNN at base pairs 229 to 231 is CAG | SEQ ID NO: 9 |
| Xaa77→Ser | NNN at base pairs 229 to 231 is AGT | SEQ ID NO: 10 |
| Xaa77→Ala | NNN at base pairs 229 to 231 is GCT | SEQ ID NO: 11 |
| Xaa77→Ser; Xaa71→Ser; Xaa72→Ser; | NNN at base pairs 229 to 231 is AGT; NNN at base pairs 211 to 213 is AGC; NNN at base pairs 214 to 216 is AGC | SEQ ID NO: 12 |
| Xaa78→Ala | NNN at base pairs 232 to 234 is GCG | SEQ ID NO: 13 |
| Xaa78→Ser | NNN at base pairs 232 to 234 is AGC | SEQ ID NO: 14 |
| Xaa77→Glu | NNN at base pairs 229 to 231 is GAG | SEQ ID NO: 15 |

Alternatively, the nucleic acids can be constructed based on chemical synthesis and/or enzymatic ligation reactions using procedures known in the art. See, for example, Sambrook et al. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acids of the invention can be incorporated into any expression vector. In this regard, the invention provides expression vectors comprising any of the nucleic acids of the invention. For purposes herein, the term "expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive expression vectors can comprise any type of nucleotides, including, but not limited to DNA and RNA, which can be single-stranded or double-stranded, synthesized or obtained in part from natural sources, and which can contain natural, non-natural or altered nucleotides. The expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The expression vector of the invention can be any suitable expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-C1, pMAM and pMAMneo (Clontech). Preferably, the expression vector is a plasmid, e.g., a bacterial plasmid.

The expression vectors of the invention can be prepared using standard recombinant DNA techniques described in, for example, Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable marker genes for the inventive expression vectors include, for instance, neomycin/G418 resistance genes, hygromycin resistance genes, histidinol resistance genes, tetracycline resistance genes, and ampicillin resistance genes.

The expression vector can comprise a native or normative promoter operably linked to the nucleotide sequence encoding the substituted EL-15 (including functional portions and functional variants thereof), or to the nucleotide sequence which is complementary to or which hybridizes to the nucleotide sequence encoding the substituted IL-15. The selection of promoters, e.g., strong, weak, is within the ordinary skill of the artisan. Similarly, the combining of a nucleotide sequence with a promoter is also within the skill of the artisan. The promoter can be a non-bacterial promoter or a bacterial promoter.

The invention further provides a host cell comprising any of the expression vectors or nucleic acid sequences described herein. As used herein, the term "host cell" refers to any type of cell that can contain the inventive expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a $E.$ $coli$ cells, Chinese hamster ovarian cells, monkey VERO cells, COS cells, HEK293 cells, and the like. Preferably, the host cell is preferably a prokaryotic cell, e.g., a DH5α cell.

Also provided by the invention is a population of cells comprising at least one host cell described herein. The population of cells can be a heterogeneous population comprising the host cell comprising any of the expression vectors described, in addition to at least one other cell which does not comprise any of the expression vectors. Alternatively, the population of cells can be a substantially homogeneous population, in which the population comprises mainly of host cells (e.g., consisting essentially of) comprising the expression vector. The population also can be a clonal population of cells, in which all cells of the population are clones of a single host cell comprising an expression vector, such that all cells of the population comprise the expression vector. In one embodiment of the invention, the population of cells is a clonal population comprising host cells comprising an expression vector as described herein.

The inventive substituted IL-15 (including functional portions and functional variants thereof), nucleic acids, expression vectors, host cells (including populations thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%. The substituted IL-15 amino acid sequences of the invention can be prepared using standard techniques known in the art such as those described in, for example, $Current$ $Protocols$ $in$ $Protein$ $Science$, John C. Wiley and Sons, 2007.

The inventive substituted IL-15, polypeptides, proteins (including functional portions and variants thereof), nucleic acids, expression vectors, host cells (including populations thereof), all of which are collectively referred to as "inventive substituted IL-15 materials" hereinafter, can be formulated into a composition, such as a pharmaceutical composition. In this regard, the invention provides a pharmaceutical composition comprising any of the substituted IL-15, polypeptides, proteins, functional portions, functional variants, nucleic acids, expression vectors, host cells (including populations thereof), and a pharmaceutically acceptable carrier. The inventive pharmaceutical compositions containing any of the inventive substituted IL-15 materials can comprise more than one inventive substituted IL-15 material, e.g., a polypeptide and a nucleic acid, or two or more different substituted IL-15 sequences. Alternatively, the pharmaceutical composition can comprise an inventive substituted IL-15 material in combination with another pharmaceutically active agents or drugs, such as, for example, chemotherapeutic agents.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive substituted IL-15 material, as well as by the particular method used to administer the inventive substituted IL-15 material. Accordingly, there are a variety of suitable formulations of the pharmaceutical composition of the invention. For example, the formulation may be suitable for oral, aerosol, parenteral, subcutaneous, intravenous, intramuscular, intraarterial, intrathecal, interperitoneal, rectal, or vaginal administration. More than one route can be used to administer the inventive substituted IL-15 materials, and in certain instances, a particular route can provide a more immediate and more effective response than another route.

For purposes of the invention, the amount or dose of the inventive IL-15 product administered should be sufficient to effect, e.g., a therapeutic or prophylactic response, in the subject or animal over a reasonable time frame. For example, the dose of the inventive IL-15 product should be sufficient to treat or prevent the condition in a period of up to 2 hours, from about 2 hours or longer, e.g., 12 to 24 or more hours, from the time of administration. In certain embodiments, the time period could be even longer. The dose will be determined by the efficacy of the particular inventive IL-15 product and the condition of the animal (e.g., human), as well as the body weight of the animal (e.g., human) to be treated.

The dose of the inventive IL-15 product also will be determined by the existence, nature and extent of any adverse side effects that might accompany the administration of a particular inventive IL-15 product. Typically, the attending physician will decide the dosage of the inventive IL-15 product with which to treat each individual patient, taking into consideration a variety of factors, such as age, body weight, general health, diet, sex, inventive IL-15 product to be administered, route of administration, and the severity of the condition being treated. By way of example and not intending to limit the invention, the dose of the inventive IL-15 product can be about 0.01 to about 2,000 μg/kg body weight of the subject being treated/day, from about 0.1 to about 200 μg/kg body weight/day, about 1 μg to about 20 μg/kg body weight/day.

With respect to the inventive methods, the condition may be any condition, including any of, for example, cancer, lymphocytopenia, immune deficiency associated with stem cell transplantation or organ transplantation; viral, bacterial, fungal, or parasitic infections such as, e.g., meningitis, pneumonia, bronchitis, human immune deficiency virus (HIV), herpes simplex virus (HSV) (e.g., HSV-1 and HSV-2), influenza, Epstein-Barr virus, cytomegalovirus (CMV), hepatitis, Dengue virus, malaria, lymphocytic choriomeningitis virus (LCMV), vesicular stomatitis virus (VSV), appendicitis, Campylobacter, rotavirus, Salmonella, Shigella adenovirus, chlamydia, diphtheria, encephalitis, gonorrhea, Listeria, Lyme disease, measles, mononucleosis, mumps, rabies, scarlet fever, smallpox, tuberculosis, Streptococcus, Staphylococcus, pinworm, giardiasis, toxoplasmosis, trichonomiasis, tetanus, and human papillomavirus. See also, Diab, A. et al., *Cytotherapy* 7(1):23-35 (2005) and Rodrigues et al., *Expert Rev. Vaccines* 8(2), 167-177 (2009).

The cancer can be any cancer, including any of, for example, acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition being treated or prevented. Also, for purposes herein, "prevention" can encompass delaying the onset of the condition, or a symptom or condition thereof.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Example 1

This example demonstrates that in vitro preparation of unsubstituted IL-15 produces a close-doublet heterogeneity in HPLC analyses.

An unsubstituted IL-15 in vitro preparation is analyzed by RP-HPLC (YMC-C4 column, 4.6 mm×150 mm, 5-μm beads, 20° C. column temperature, at 0.9 mL/minute flow rate, load at 0% ethanol, elution by 42-77% linear gradient of ethanol in water with 20 mM ammonium acetate: acetate, 0.2 mM $CaCl_2$ buffer, pH approximately 5, conducted over 21 column volumes). The resulting chromatogram is shown in FIG. 1.

Deamidation by-products may be observed as a close-doublet heterogeneity. In FIG. 1, the close-doublet includes the peaks at 84.36 and 86.74. The peak at 86.74 corresponds to undeamidated IL-15, and the peak at 84.36 corresponds to deamidated IL-15. The peak at 84.36 includes D- and L-isoaspartic acid and D- and L-aspartic acid deamidation by-products of IL-15.

Example 2

This example demonstrates that the close-doublet heterogeneity includes undeamidated IL-15 and deamidation by-products of IL-15.

Figure 2:
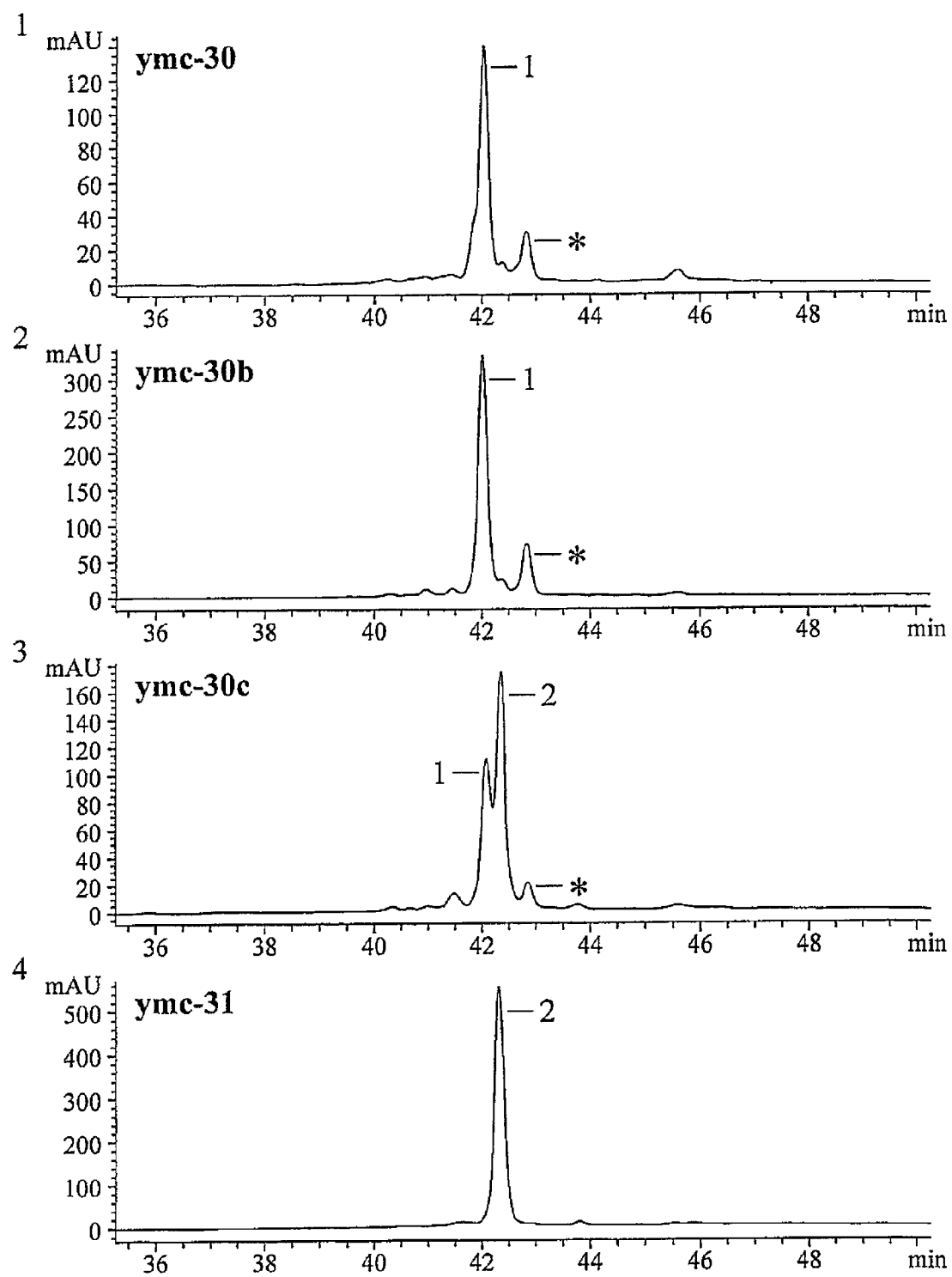
FIG. 2 shows chromatograms from an RP-HPLC analysis of respective fractions obtained from the separation shown in FIG. 1 (Waters X-Bridge BEH300 column, 4.6 mm×250 mm, 3.5 μm beads, 20° C. column temperature, 10 mL/minute flow rate, load at 0% acetonitrile, elution by 35-65% linear gradient of acetonitrile in water with 0.1% TFA ion-pairing agent, pH approximately 2, conducted over 12 column volumes).

The close-doublet heterogeneity observed in Example 1 is further sub-fractionated into four regions YMC-30, YMC 30-b, YMC-30c, and YMC-31, as shown in FIG. 1. Each of these four regions is further analyzed by RP-HPLC (Waters X-Bridge BEH300 column, 4.6 mm×250 mm, 3.5 μm beads, 20° C. column temperature, 1.0 mL/minute flow rate, load at 0% acetonitrile, elution by 35-65% linear gradient of acetonitrile in water with 0.1% TFA ion-pairing agent, pH approximately 2, conducted over 12 column volumes). As shown in FIG. 2, the close-doublet heterogeneity includes Peak 1, Peak 2, and Peak *. Peak 1 corresponds to the D-, L-isoaspartic acid deamidation by-product, Peak * corresponds to the D-, L-aspartic acid deamidation by-product, and Peak 2 corresponds to undeamidated IL-15. Thus, in vitro preparations of unsubstituted IL-15 include undeamidated IL-15 as well as the deamidation by-products D-, L-isoaspartic acid and L-aspartic acid.

Example 3

This example demonstrates that the close-doublet heterogeneity includes undeamidated IL-15 and deamidation by-products of IL-15.

Figure 3:
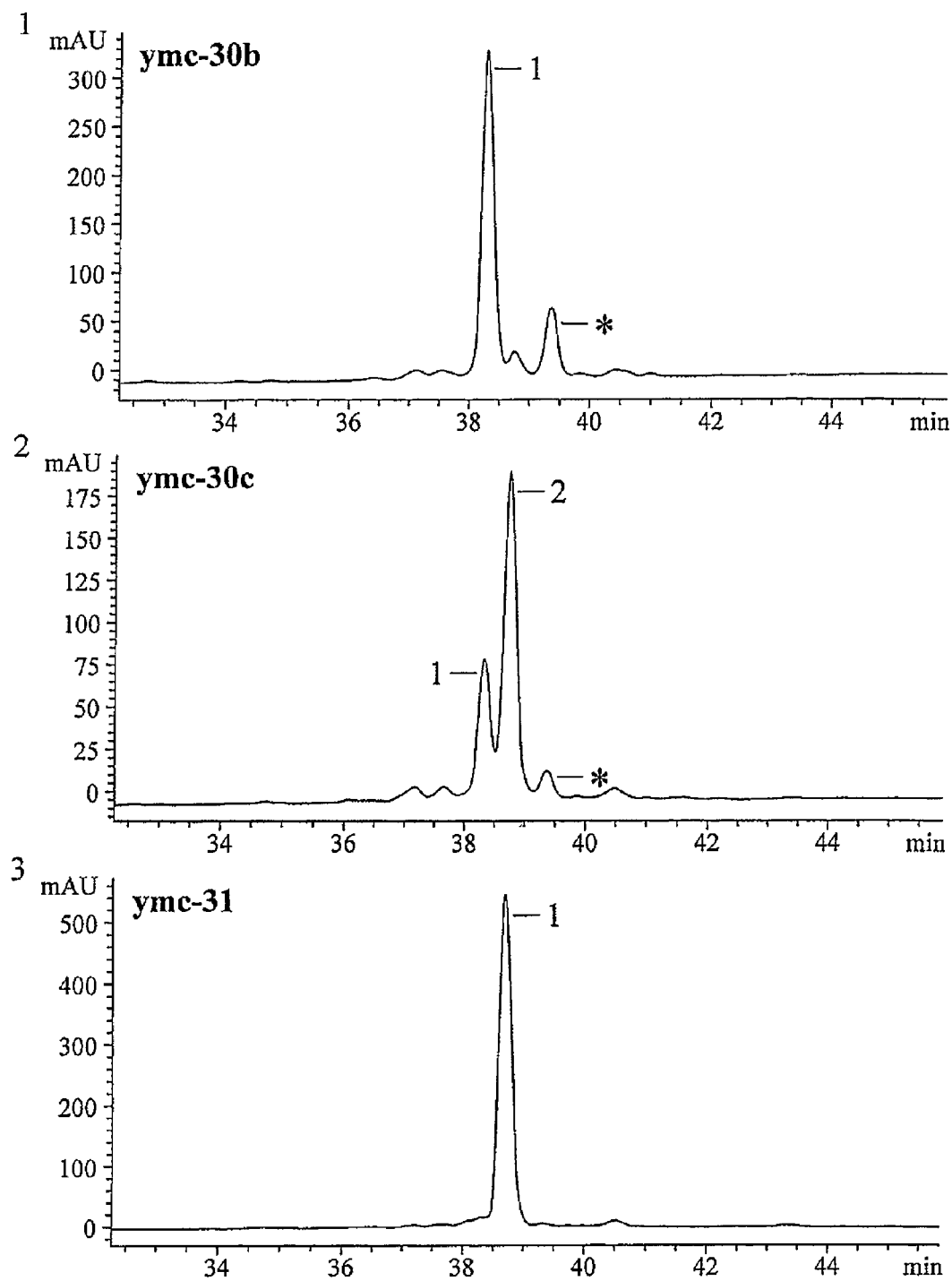
FIG. 3 shows chromatograms from an RP-HPLC analysis of respective fractions obtained from the separation shown in FIG. 1 (Waters YMC-C4 column, 4.6 mm×150 mm, 5-μm beads, 20° C. column temperature, 1.0 mL/minute flow rate, load at 0% acetonitrile, elution by 35-65% linear gradient of acetonitrile in water with 0.1% TFA ion-pairing agent, pH approximately 2, conducted over 22 column volumes).

Regions YMC 30-b, YMC-30c, and YMC-31 are analyzed by RP-HPLC (Waters YMC-C4 column, 4.6 mm×150 mm, 5-μm beads, 20° C. column temperature, 1.0 mL/minute flow rate, load at 0% acetonitrile, elution by 35-65% linear gradient of acetonitrile in water with 0.1% TFA ion-pairing agent, pH approximately 2, conducted over 22 column volumes). As shown in FIG. 3, the close-doublet heterogeneity includes Peak 1, Peak 2, and Peak *. Peak 1 corresponds to the D-, L-isoaspartic acid deamidation by-product, Peak * corresponds to the D-, L-aspartic acid deamidation by-product, and Peak 2 corresponds to undeamidated IL-15. Thus, in vitro preparations of unsubstituted IL-15 include undeamidated IL-15 as well as the deamidation by-products D-, L-isoaspartic acid and D-, L-aspartic acid.

Example 4

This example demonstrates that the order of elution of deamidated IL-15 and undeamidated IL-15 in an RP-HPLC analysis reverses in an anion exchange HPLC analysis, which is consistent with the deamidation of IL-15.

Figure 4:
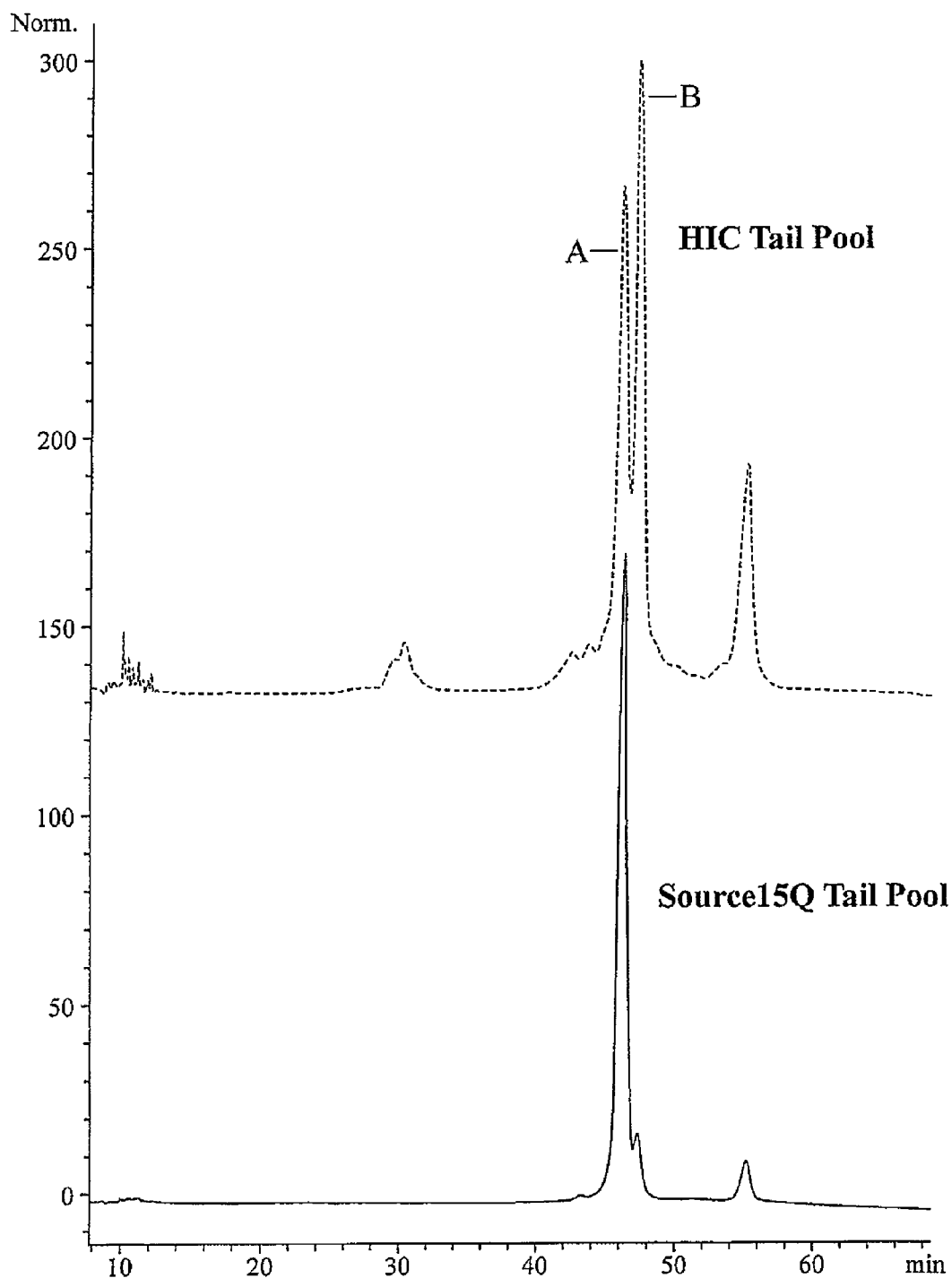
FIG. 4 shows chromatograms from an RP-HPLC analysis of two unsubstituted IL-15 preparations of a process sample following purification by preparative hydrophobic interaction chromatography (HIC Tail Pool) and a process sample following purification by preparative ion-exchange chromatography (Source15Q Tail Pool) (analysis over Waters YMC-C4 column, 4.6 mm×150 mm, 5-μm beads, 20° C. column temperature, 0.9 mL/minute flow rate, load at 0% acetonitrile, elution by 50-72% linear gradient of ethanol in water with 20 mM 20 mM ammonium acetate:acetate, 0.2 mM $CaCl_2$ buffer, pH approximately 5, conducted over 21 column volumes).

An unsubstituted IL-15 preparation is analyzed by RP-HPLC (analysis over Waters YMC-C4 column, 4.6 mm×150 mm, 5-μm beads, 20° C. column temperature, 0.9 mL/minute flow rate, load at 0% acetonitrile, elution by 50-72% linear gradient of ethanol in water with 20 mM 20 mM ammonium acetate:acetate, 0.2 mM $CaCl_2$ buffer, pH approximately 5, conducted over 21 column volumes). The resulting chromatograph is shown in FIG. 4. Peak A, which corresponds with deamidated IL-15, elutes before Peak B, which corresponds with undeamidated IL-15.

Figure 5:
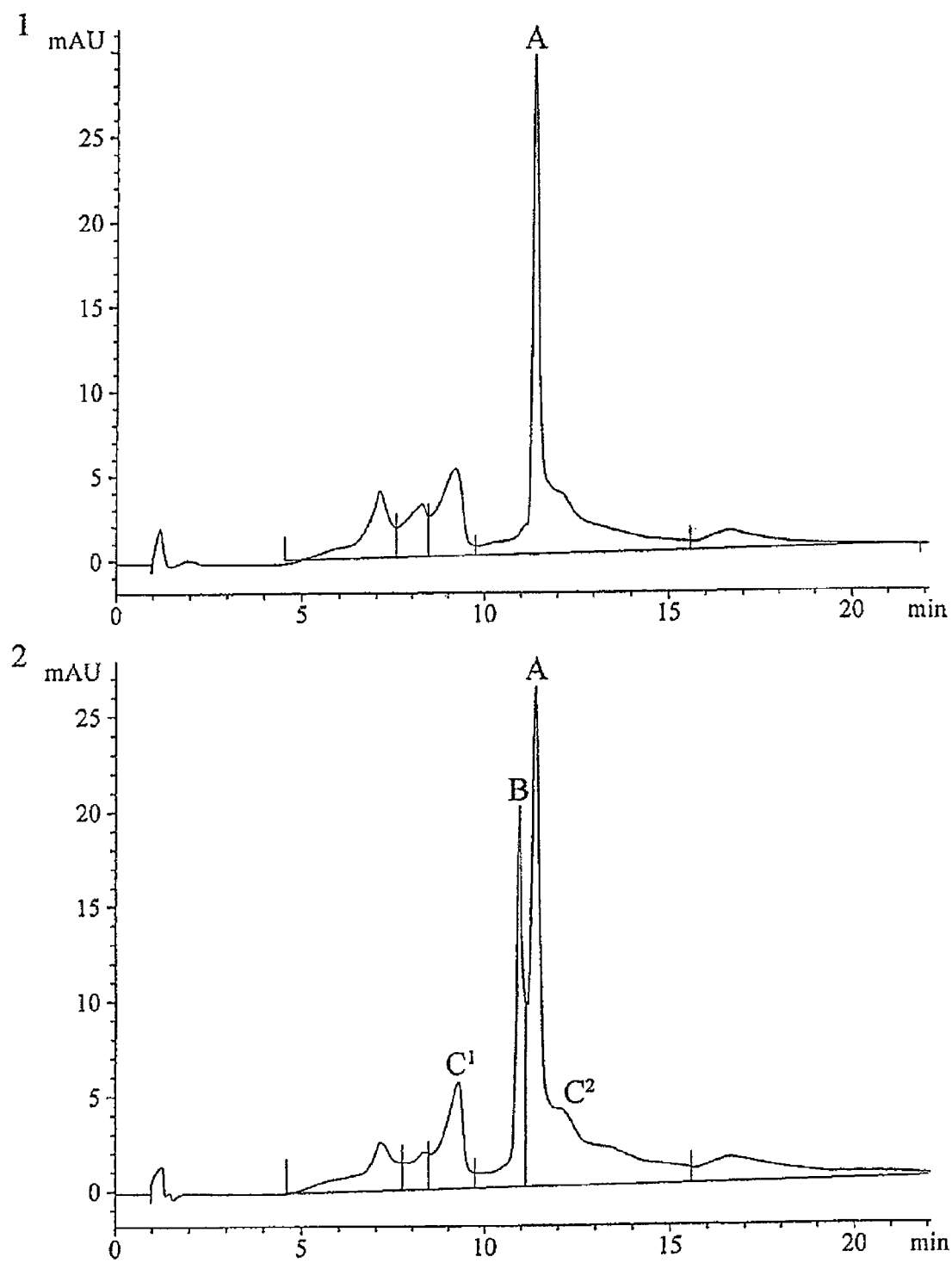
FIG. 5 shows a chromatogram from a ProPac Anion Exchange-HPLC analysis of two unsubstituted IL-15 preparations of an upstream process sample following purification by preparative hydrophobic interaction chromatography (HIC Tail Pool; Panel 2) and a process sample following purification by preparative ion-exchange chromatography (Source15Q Tail Pool; Panel 1) (analysis over Waters ProPac-SAX-10, elution by linear gradient from 7-700 mM NaCl in a mobile phase containing ~10 mM Bis-Tris-Propane, 30% ethanol buffer, pH approximately 7.4, measured prior to ethanol addition).

The unsubstituted IL-15 preparation is also analyzed by anion exchange HPLC (analysis over Waters ProPac-SAX-10, elution by linear gradient from 7-700 mM NaCl in a mobile phase containing ~10 mM Bis-Tris-Propane, 30% ethanol buffer, pH approximately 7.4, measured prior to ethanol addition). The resulting chromatogram is shown in FIG. 5. Peak A, which corresponds with deamidated IL-15, elutes after Peak B, which corresponds with undeamidated IL-15.

Thus, the order of elution between the deamidated and undeamidated IL-15 is reversed between RP-HPLC and anion-exchange HPLC. These results are consistent with the deamidation of IL-15. Because deamidation replaces the neutral amide group of asparagine with a negatively charged, less hydrophobic, more polar carboxylic acid side chain of aspartic acid, the deamidated form of IL-15 has a greater attraction to the anion-exchange column. Therefore, the deamidated form of IL-15 elutes later than the undeamidated form of IL-15 on an anion exchange column.

Example 5

This example demonstrates that unsubstituted IL-15 in vitro preparations includes isoaspartic acid, a deamidation by-product of IL-15.

An unsubstituted IL-15 in vitro preparation is digested with Protein Isoaspartyl Methyltransferase (PIMT) enzyme using an Isoquant™ Protein Deamidation Detection kit from Promega Corporation (Madison, Wis., U.S.A.) according to the manufacturer's directions, with the exception that the buffer provided in the kit is replaced with an identical buffer that does not include detergents.

Figure 6:
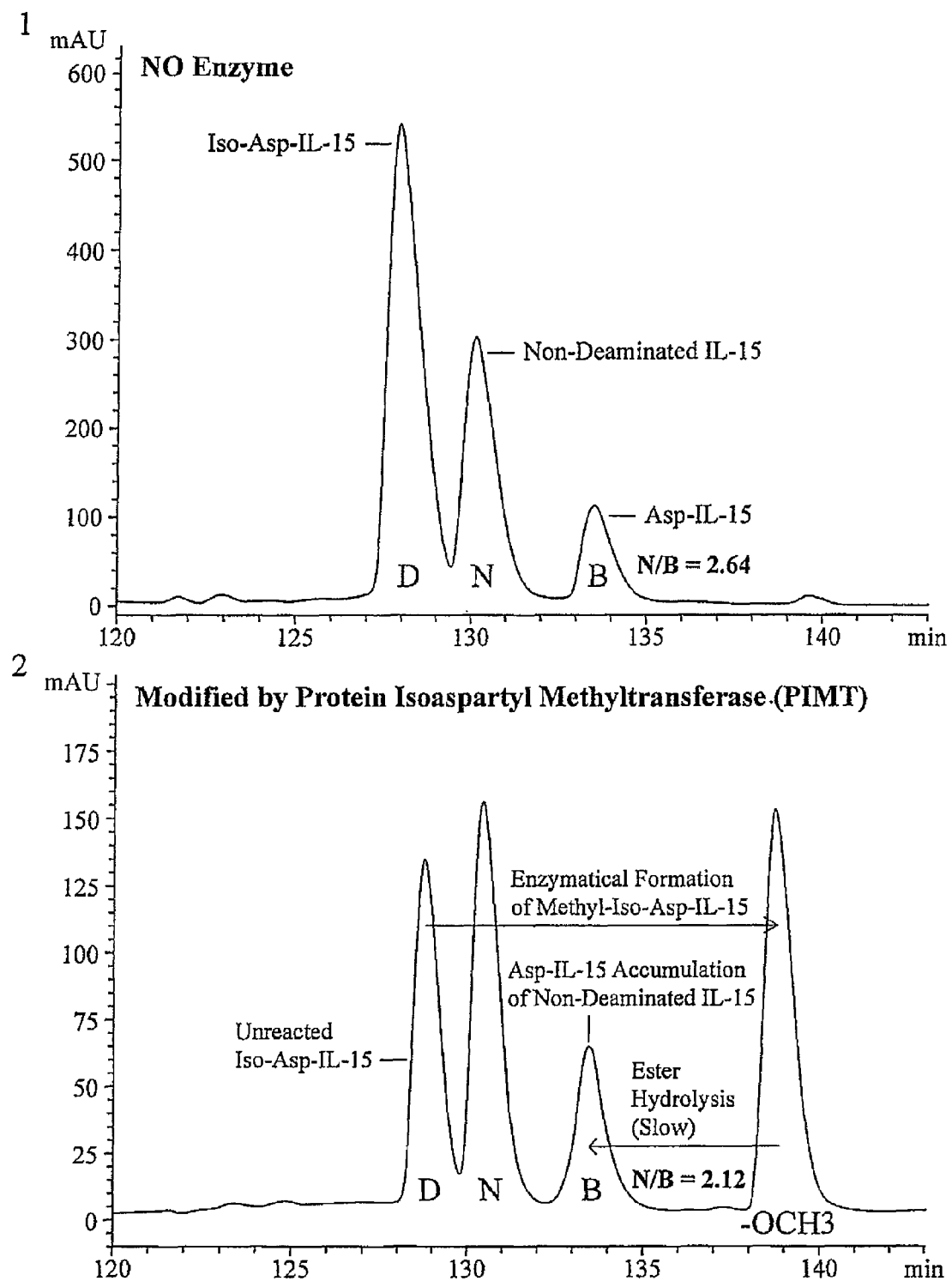
FIG. 6 shows chromatograms from an RP-HPLC analysis of an unsubstituted IL-15 preparation before and after methylation of deamidation-produced isoaspartate residues using Protein Isoaspartyl Methyltransferase (PIMT) enzyme in the presence of the methyl group donor S-Andenosyl-L-Methionine.

The IL-15 preparation is fractionated by size exclusion chromatography SEC-ExRP-HPLC (guard column) to remove aggregates, detergents and salts and to select for IL-15. The IL-15 protein-containing pool is analyzed by RP-HPLC (Tandem X-Bridge BEH300 column, 2.1×250 mm, 3.5 μm beads, water/acetonitrile/0.08% TFA/formic acid buffer, 50 μl in 250 μl final volume, 48-53% over 100 minutes, 20° C., 0.16 ml per minute). The results are shown in FIG. 6. The upper panel of FIG. 6 shows the undigested unsubstituted IL-15 preparation, with peaks D, N, and B corresponding to the iso-aspartic acid deamidation product of IL-15, the undeamidated IL-15, and the aspartic acid deamidation product of IL-15, respectively.

The PIMT enzyme selectively methylates iso-aspartic acid with methyl group donation by S-adenosyl methionine. As shown in the lower panel of FIG. 6, a new peak appears on the right following digestion of the unsubstituted IL-15 preparation with the PIMT enzyme, which corresponds to the enzymatically formed methyl-iso-aspartic acid deamidation by-product of IL-15. Thus, in vitro preparations of unsubstituted IL-15 include one of the by-products of deamidation of IL-15, i.e., the iso-aspartic acid version of IL-15.

Example 6

An unsubstituted, deamidation enriched recombinant human IL-15 sample, having between 60-70% deamidation as determined analytically by RP-HPLC, is digested with chymotrypsin. The resulting digest is reduced with dithiothreitol (DTT). The chymotryptic peptides are separated by reverse phase HPLC with UV and mass spectral detection. Using a MicroMass Q-ToF API US, quadrapole time-of-flight mass spectrometer (Waters, Inc., Milford, Mass.), mass spectrometric detection is achieved by positive ion ESI-MS with selected peptides further analyzed by on-line ESI-MS/MS.

Figure 7:
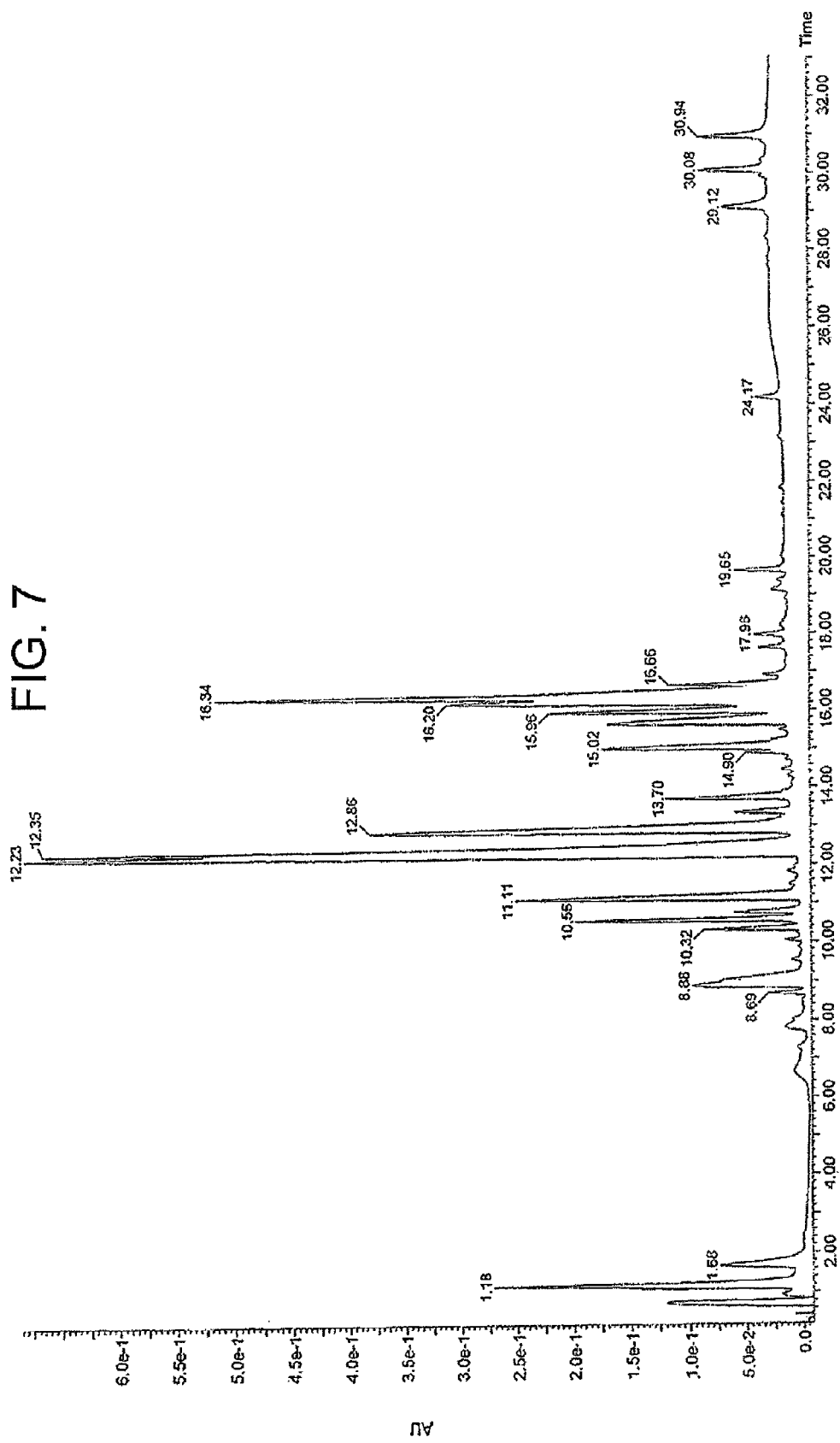
FIG. 7 shows an RP-HPLC analysis of peptides resulting from a chymotrypsin digest of deamidation enriched human IL-15.

The resulting reverse phase HPLC chromatogram is shown in FIG. 7 and Table 4. FIG. 7 and Table 4 summarize the relative elution positions for a subset of peptides that cover all of the asparagines within the deamidation enriched IL-15 sample.

TABLE 4

| Retention Time (min.) | Possible Assignment of Asn Containing Peptides |
|---|---|
| 1.1 | I(111)-S(114) |
| 10.0 | E(53)-N(65) |
| 12.2 | M(0)-W(2) |
| 13.7 | E(53)-L(66) |
| 16.0 | S(75)-F(99) |
| 16.3 | A(70)-F(99) deamidated |
| 16.5 | S(73)-F(99) (shoulder) |
| 16.9 | Q(48)-L(66) |
| 17.6 | I(67)-F(99) deamidated or I(68)-L(100) deamidated |
| 19.1 | E(53)-L(69) |

The asparagine residue-containing peptides are found to remain predominantly non-deamidated. Specifically noted are [peak: peptide] species [16.0: S(75)-F(99)] and [16.5: S(73)-F(99)], both of which include the N(77) modification site, but have unmodified asparagines residues at N(77). The detection of these two specific non-deamidated peptides and the balance of remaining non-deamidated peptides demonstrates that the digestion, chromatography and mass spectrophotometric detection methods are sufficiently gentle to preserve non-deamidated peptides.

However, deamidation is observed in a narrow subset of peptides. Specifically noted are [peak: peptide] species [16.3: A(70)-F(99)-deamidated] and [17.6: I(67)-F(99)-deamidated or 17.6: I(68)-L(100)-deamidated]. Because the [16.3: A(70)-F(99)] peptide sequence contains five asparagine residues, all within an peptide of convenient size, the peptide provides an ideal empirical basis on which to detect possible deamidation at the N(71), N(72), N(77), and N(79) and N(95) sites. If the peptide is deamidated, it would be expected to have a molecular mass that is one atomic mass unit more than a peptide that is not deamidated. Further, the 1101.80 mass-to-charge ratio of this peptide is consistent with a single deamidation event resulting in a parent monoisotopic molecular mass of 3303.4. This empirical measurement agrees with the theoretical monoisotopic molecular mass calculated for a deamidated form of peptide A(70)-F(99) where the expected value is 3303.4628 atomic mass units.

This example demonstrated that deamidation occurs within the A(70) to F(99) peptide fragment of unsubstituted IL-15 (SEQ ID NO: 7).

Example 7

Figure 8:
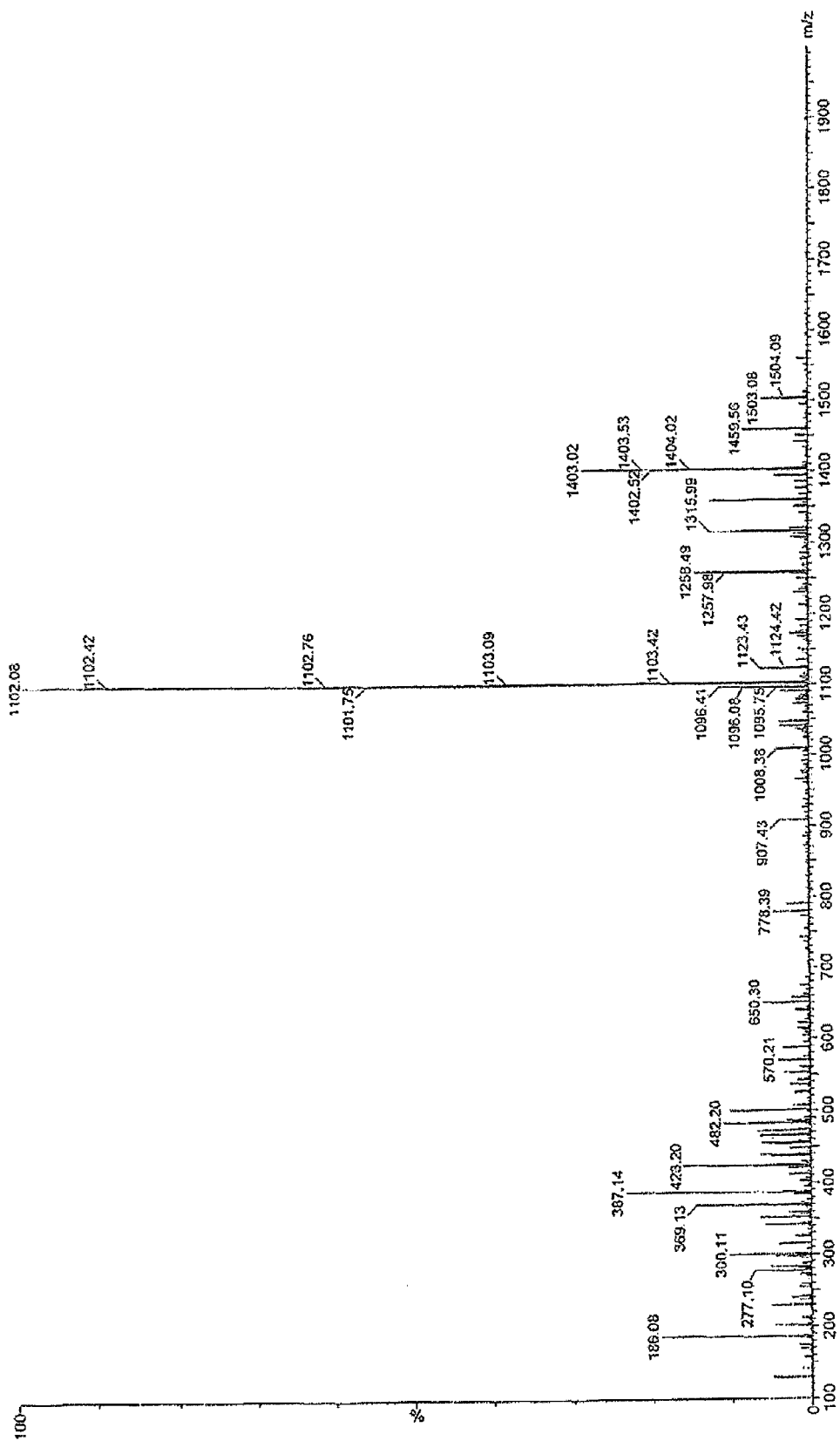
FIG. 8 shows a wide mass-range view of the fragmentation mass spectrum obtained from MS/MS analysis of a deamidation enriched IL-15 chymotryptic peptide having a mass to charge ratio of 1101.80 atomic mass units and a singly-protonated monoisotopic molecular weight of 3303.4 atomic mass units that eluted at 16.3 minutes in FIG. 7.
Figure 9:
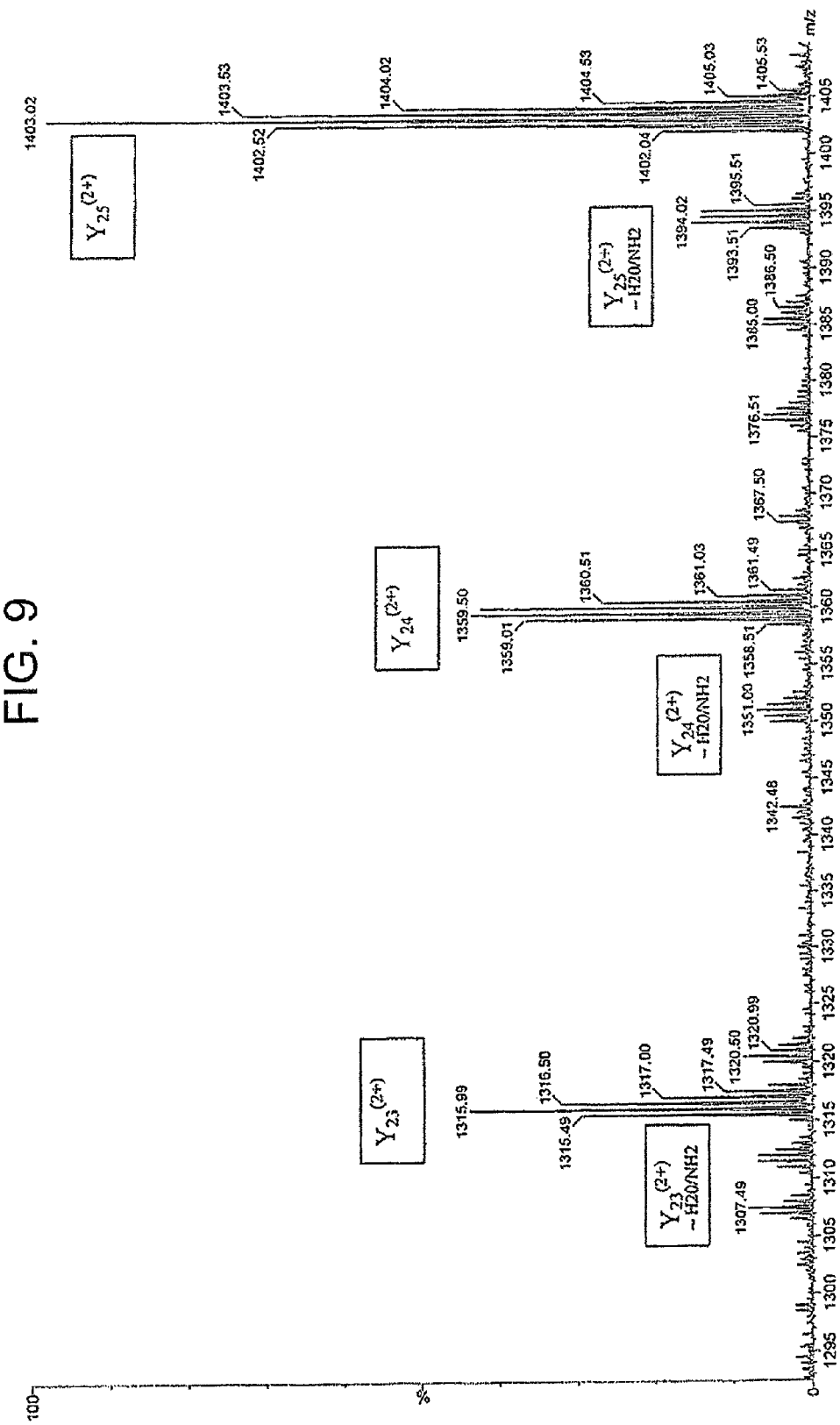
FIG. 9 shows a narrow mass-range view of the fragmentation mass spectrum obtained from MS/MS analysis of a deamidation enriched IL-15 chymotryptic peptide having a mass to charge ratio of 1101.80 atomic mass units and a singly-protonated monoisotopic molecular weight of 3303.4 atomic mass units that eluted at 16.3 minutes in FIG. 7.

The A(70)-F(99) peptide of Example 6 corresponding to an on-line mass of 1101.80 atomic mass units is subjected to in-detector, collisional-fragmentation (LC-MS/MS). The results are shown in FIGS. 8 and 9 and Table 5.

TABLE 5 rHu-IL-15 Peptide MS/MS for Species at 1101.80 ES+ [16.356: (A70)-F(99)]
Within each isotopic envelope, the peak corresponding to the most abundant
peak ion minus one molucular weight unit was assinged as the monoisotopic peak.

| Fragment a | ID | Calcualted a | Observed a | | Fragment b | ID | Calculated b | Observed b | | Fragment y | ID | Calculated y | Observed y | |
|---|---|---|---|---|---|---|---|---|---|---|---|---|---|---|
| 1 | A | — | N/M | | 1 | A | — | N/M | | 30 | A | — | N/M | |
| 2 | N | 158.0924 | 158.08 | (+1) | 2 | N | 186.0873 | 186.08 | (+1) | 29 | N | 3232.4256 | N/M | (+2) |
| 3 | N | 272.1353 | 272.13 | (+1) | 3 | N | 300.1302 | 300.11 | (+1) | 28 | N | 3118.3827 | 3118.18 | (+2) |
| 4 | S | 359.1674 | 359.15 | (+1) | 4 | S | 387.1623 | 387.14 | (+1) | 27 | S | 3004.3398 | 3004.14 | (+2) |
| 5 | L | 472.2514 | 472.22 | (+1) | 5 | L | 500.2463 | 500.22 | (+1) | 26 | L | 2917.3078 | 2917.14 | (+2) |
| 6 | S | 559.2835 | 560.19 | (+1) | 6 | S | 587.2784 | 587.24 | (+1) | 25 | S | 2804.2237 | 2803.80 | (+2) |
| 7 | S | 646.3155 | 674.27 | (+1) | 7 | S | 674.3104 | (691.21) | (+1) | 24 | S | 2717.1917 | 2717.02 | (+2) |
| 8 | D | 761.3424 | 761.39 | (+1) | 8 | D | 789.3373 | 789.28 | (+1) | 23 | D | 2630.1596 | 2629.98 | (+2) |
| 9 | G | 818.3639 | 818.30 | (+1) | 9 | G | 846.3588 | 846.30 | (+1) | 22 | G | 2515.1327 | 2514.96 | (+2) |
| 10 | N | 932.4068 | (935.67) | (+1) | 10 | N | 960.4017 | 960.33 | (+1) | 21 | N | 2458.1112 | 2457.96 | (+2) |
| 11 | V | 1031.4752 | N/M | | 11 | V | 1059.4701 | N/M | | 20 | V | 2344.0683 | 2343.90 | (+2) |
| 12 | T | 1132.5229 | N/M | | 12 | T | 1160.5178 | N/M | | 19 | T | 2244.9999 | 2244.88 | (+2) |
| 13 | E | 1261.5655 | N/M | | 13 | E | 1289.5604 | N/M | | 18 | E | 2143.9522 | 2143.90 | (+2) |
| 14 | S | 1348.5975 | N/M | | 14 | S | 1376.5924 | N/M | | 17 | S | 2014.9096 | 2014.78 | (+2) |
| 15 | G | 1405.619 | N/M | | 15 | G | 1433.6139 | N/M | | 16 | G | 1927.8776 | 1927.72 | (+2) |
| 16 | C | 1508.6282 | N/M | | 16 | C | 1536.6231 | N/M | | 15 | C | 1870.8561 | 1869.72 | (+2) |
| 17 | K | 1636.7231 | N/M | | 17 | K | 1664.7181 | N/M | | 14 | K | 1767.8469 | 1767.80 | (+2) |
| 18 | E | 1765.7657 | N/M | | 18 | E | 1793.7606 | N/M | | 13 | E | 1639.752 | 1639.64 | (+2) |
| 19 | C | 1868.7749 | N/M | | 19 | C | 1896.7698 | N/M | | 12 | C | 1510.7094 | 1510.56 | (+2) |
| 20 | E | 1997.8175 | N/M | | 20 | E | 2025.8124 | N/M | | 11 | E | 1407.7002 | N/M | (+1) |
| 21 | E | 2126.8601 | N/M | | 21 | E | 2154.855 | N/M | | 10 | E | 1278.6576 | N/M | (+1) |
| 22 | L | 2239.9442 | N/M | | 22 | L | 2267.9391 | 2267.82 | (+2) | 9 | L | 1149.615 | N/M | (+1) |
| 23 | E | 2368.9868 | N/M | | 23 | E | 2396.9817 | 2379.86 | (+2) | 8 | E | 1036.531 | N/M | (+1) |
| 24 | E | 2498.0294 | N/M | | 24 | E | 2526.0243 | 2509.94 | (+2) | 7 | E | 907.4884 | 907.43 | (+1) |
| 25 | K | 2626.1243 | N/M | | 25 | K | 2654.1192 | N/M | | 6 | K | 778.4458 | 778.39 | (+1) |
| 26 | N | 2740.1672 | N/M | | 26 | N | 2768.1622 | N/M | | 5 | N | 650.3508 | 650.30 | (+1) |
| 27 | I | 2853.2513 | N/M | | 27 | I | 2881.2462 | N/M | | 4 | I | 536.3079 | (536.27) | (+1) |
| 28 | K | 2981.3463 | N/M | | 28 | K | 3009.3412 | N/M | | 3 | K | 423.2238 | 423.20 | (+1) |
| 29 | E | 3110.3889 | N/M | | 29 | E | 3138.3838 | N/M | | 2 | E | 295.1288 | N/M | |
| 30 | F | — | N/M | | 30 | F | — | N/M | | 1 | F | 166.0863 | N/M | |

The resulting set of observed a-type, b-type and y-type fragment mass-to-charge ratios, when converted singly-protonated monoisotopic masses (based upon determination of ion-charge using observed isotopic pattern spacing) matches the theoretical calculated values for the peptide containing an aspartic acid in place of asparagine 77. The theoretical calculated values are obtained from Protein Prospector (University of California at San Francisco) MS-Product and MS-Isotope programs. It is noted that portions of the data set are consistent with co-elution of possible trace levels of non-deamidated species, species containing single-deamidation modifications in some combination of the other four possible sites within the A(70)-F(99) sequence, as well as the existence of minor species containing doubly-deamidated peptides. Thus, the possibility of other minor deamidation sites can not be ruled out by this analysis.

However, based upon the totality of the empirical evidence obtained through LC-MS/MS chymotrypic peptide map analysis, it is concluded that N(77) is the primary deamidation site within unsubstituted IL-15.

This example demonstrated that deamidation occurs at the N(77) site of unsubstituted IL-15 (SEQ ID NO: 7).

Example 8

This example demonstrates that substituted IL-15 has improved stability as compared to unsubstituted IL-15.

Genetic constructs expressing five recombinant human (rh) IL-15 site-directed substitutions were made using PCR-based site-direct mutagenesis. One construct expressed IL-15 with three substitutions (N71S/N72A/N77A). Four other genetic constructs expressed IL-15 with single-site amino acid substitutions (N77A, N77S, N77Q, or G78A). The primers used to make the constructs were as follows: N77A: SEQ ID NO: 16 (top) and SEQ ID NO: 17 (bottom); N77S: SEQ ID NO: 18 (top) and SEQ ID NO: 19 (bottom); N77Q: SEQ ID NO: (top) and SEQ ID NO: 21 (bottom); G78A: SEQ ID NO: 22 (top) and SEQ ID NO: 23 (bottom); and N71S/N72A/N77A: SEQ ID NO: 24 (top) and SEQ ID NO: 25 (bottom). The sequences of the genetic constructs were confirmed by direct sequencing after directed mutagenesis.

The unsubstituted IL-15 and the five substituted IL-15 constructs were expressed in E. coli strain BL-21 AI. The resulting IL-15 inclusion bodies were processed identically, but separately. Briefly, each substituted IL-15 was solubilized from inclusion bodies with guanidine hydrochloride and dithiothreitol; fractionated using size exclusion chromatography; refolded by dilution; and purified using hydrophobic interaction chromatography (HIC) and ion exchange (IEX) chromatography. The resulting IL-15 preparations (0.275±0.050 mg/mL, formulated in 50 mM Tris, 150 mM NaCl, 1 mM EDTA, pH 7.4) were 0.2-micron filtered; aseptically filled into autoclaved HPLC injection vials; and stored below −70° C.

Samples from the six IL-15 preparations were tested to confirm their purities and identities. Each preparation migrated on sodium dodecyl sulfate polyacrylamide gel electrophoresis (SDS-PAGE) gels as a single band in a similar position as the IL-15 reference standard and elated from a size exclusion (SEC) high performance liquid chromatography (HPLC) column as one major protein peak. Each preparation eluted from a reverse phase (RP)-HPLC column (Tandem C18 Poroshell) predominantly in one major peak (FIGS. 10A, 11A, 12A, 13A, 14A, and 15A). The desired genetic substitution for each preparation was continued versus the expected molecular weight differences that were measured using RP-electrospray ionization (ESI)-mass spectrometry (MS) analysis (Table 6).

TABLE 6

Substituted IL-15 Identity Confirmation Based on Molecular Weights

| | Expected | Actual | | Difference = Actual − Expected | | Identity |
|---|---|---|---|---|---|---|
| | (AMU) | RP-ESI-MS | RP-ESI-MS | RP-ESI-MS | RP-ESI--MS | Confirmed? |
| Unsubstituted | 12900.70 | 12898.34 | 12899.90 | −2.36 | −0.80 | Yes |
| N77A | 12857.68 | 12855.91 | — | −1.77 | — | Yes |
| N77S | 12873.68 | 12872.00 | — | −1.68 | — | Yes |
| N77Q[1] | 12914.73 | 12913.00 | 12914.19 | −1.73 | −0.54 | Yes |
| G78A[1] | 12914.73 | 12912.80 | 12914.82 | −1.93 | 0.09 | Yes |
| N71S/N72A/N77A | 12787.60 | 12786.17 | 12787.87 | −1.43 | 0.27 | Yes |

[1]N77Q and G78A are isobaric variants. These cell banks were created during different months to ensure strain fidelity.

On the basis of this characterization, the six preparations were determined to be suitable for accelerated degradation testing.

Figure 10A:
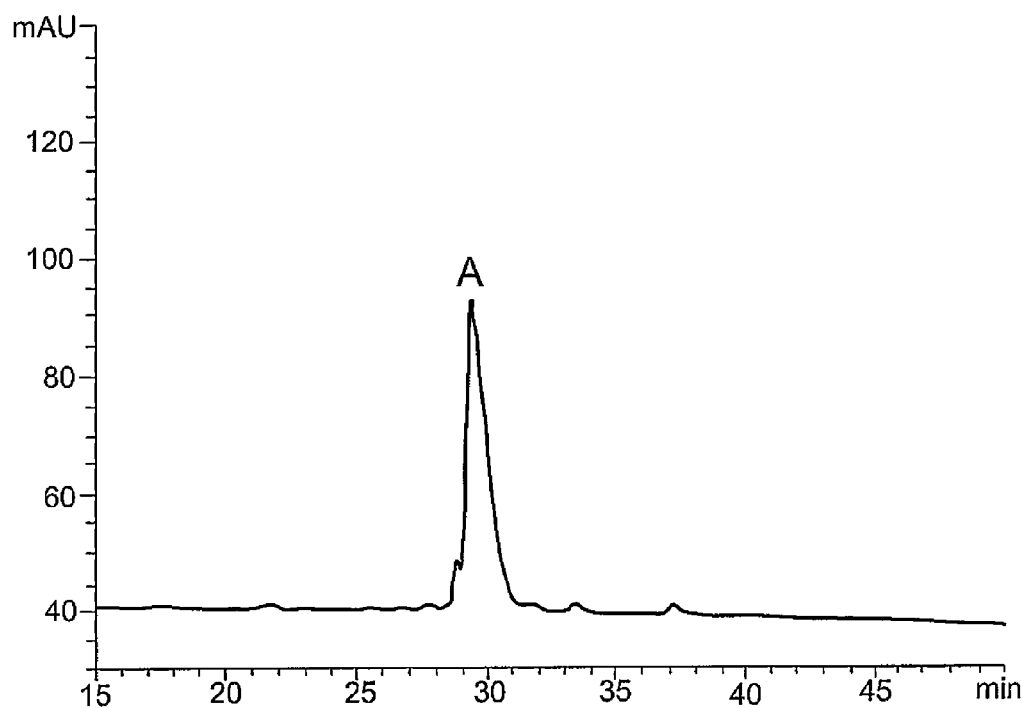
FIG. 10A shows a chromatogram from an RP-HPLC analysis of unsubstituted IL-15 prior to incubation at 37° C. for one week. "A" indicates the peak corresponding to non-degraded IL-15.
Figure 10B:
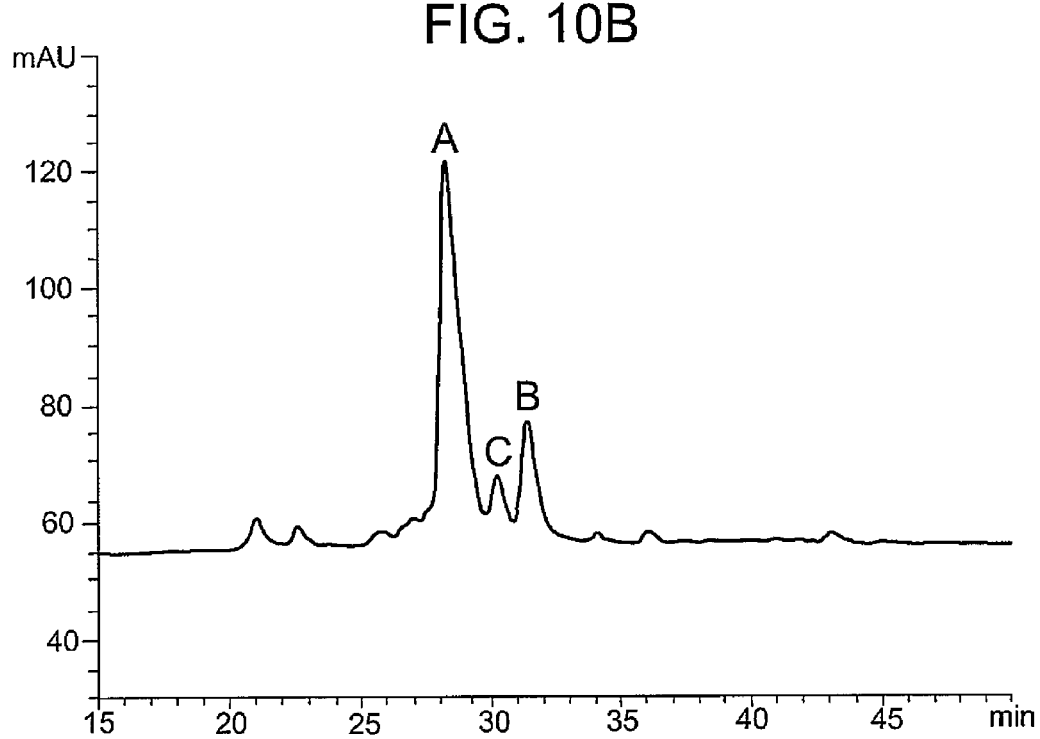
FIG. 10B shows a chromatogram from an RP-HPLC analysis of unsubstituted IL-15 following incubation at 37° C. for one week. "A," "B," and "C" indicate peaks corresponding to deamidated IL-15.
Figure 11A:
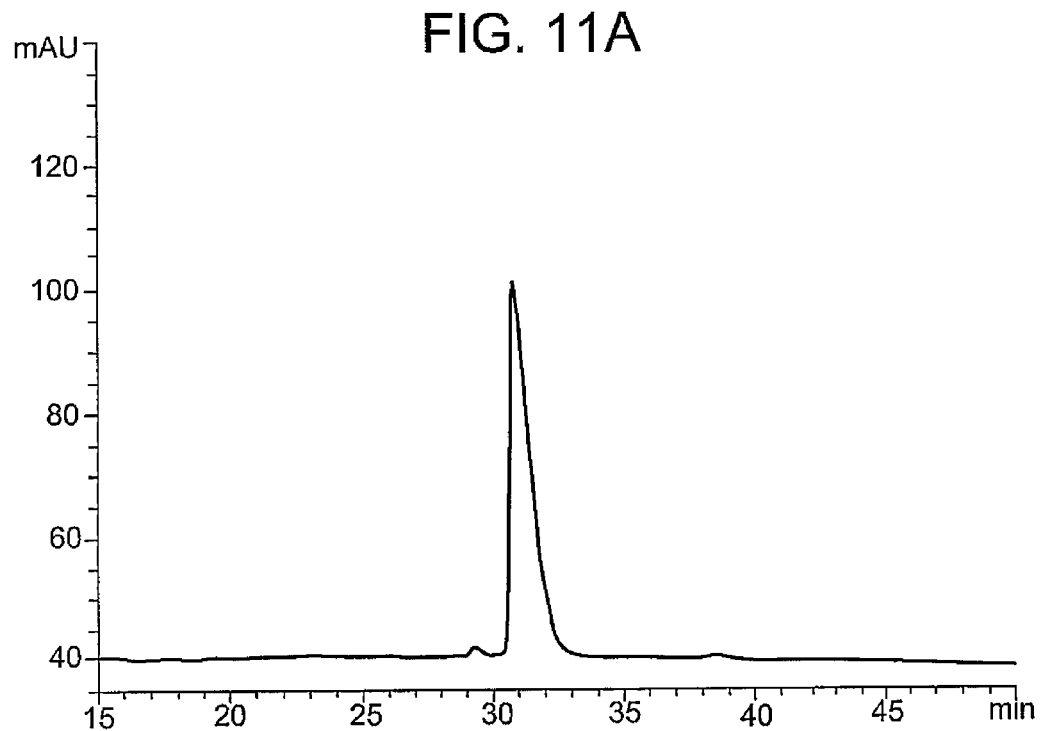
FIG. 11A shows a chromatogram from an RP-HPLC analysis of N77A substituted IL-15 prior to incubation at 37° C. for one week.
Figure 11B:
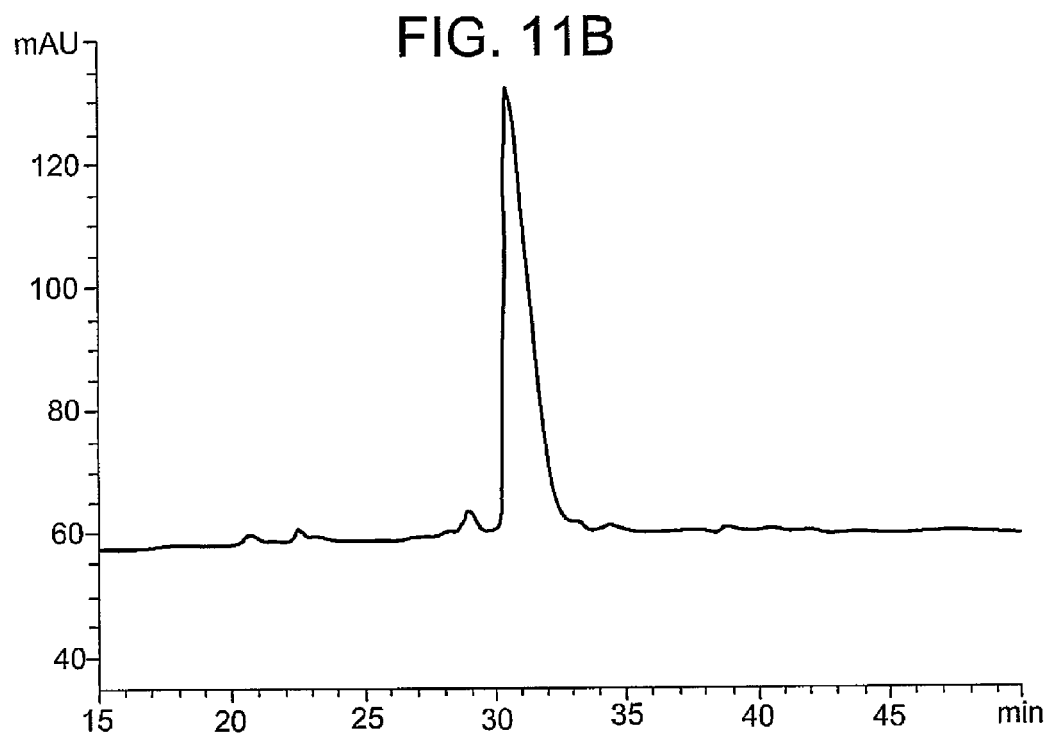
FIG. 11B shows a chromatogram from an RP-HPLC analysis of N77A substituted IL-15 following incubation at 37° C. for one week.
Figure 12A:
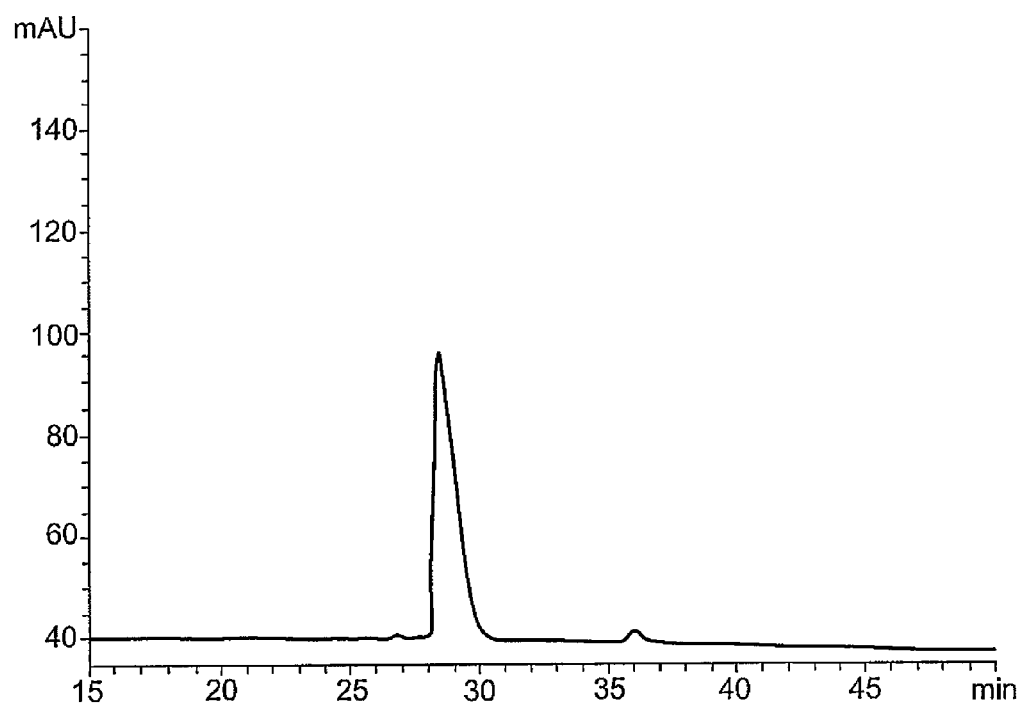
FIG. 12A shows a chromatogram from an RP-HPLC analysis of N77S substituted IL-15 prior to incubation at 37° C. for one week.
Figure 12B:
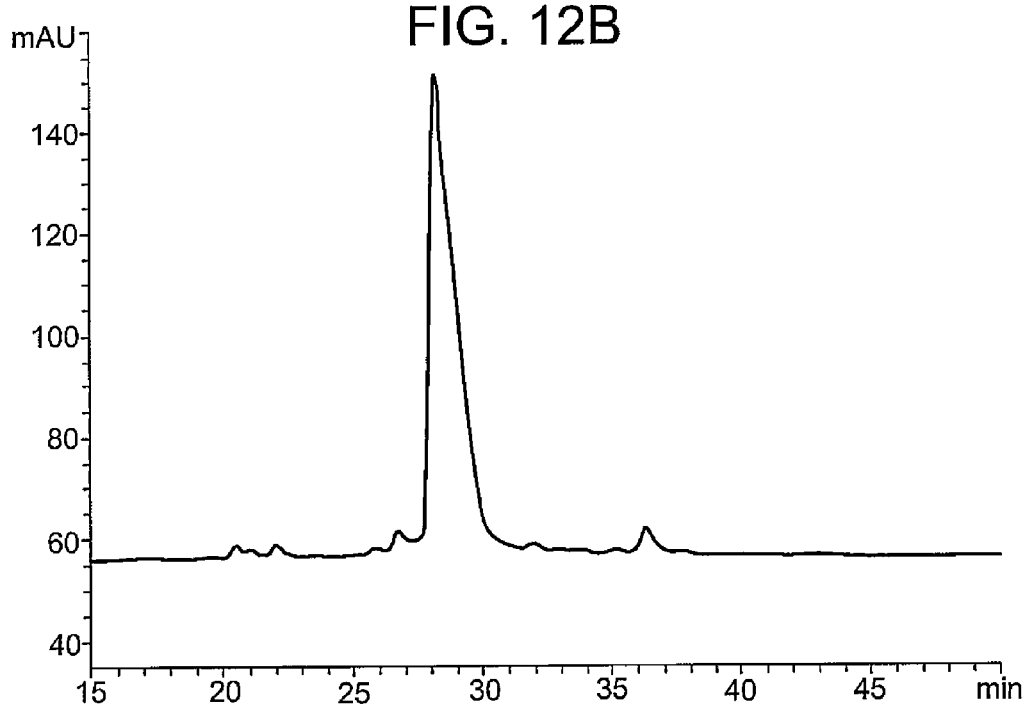
FIG. 12B shows a chromatogram from an RP-HPLC analysis of N77S substituted IL-15 following incubation at 37° C. for one week.
Figure 13A:
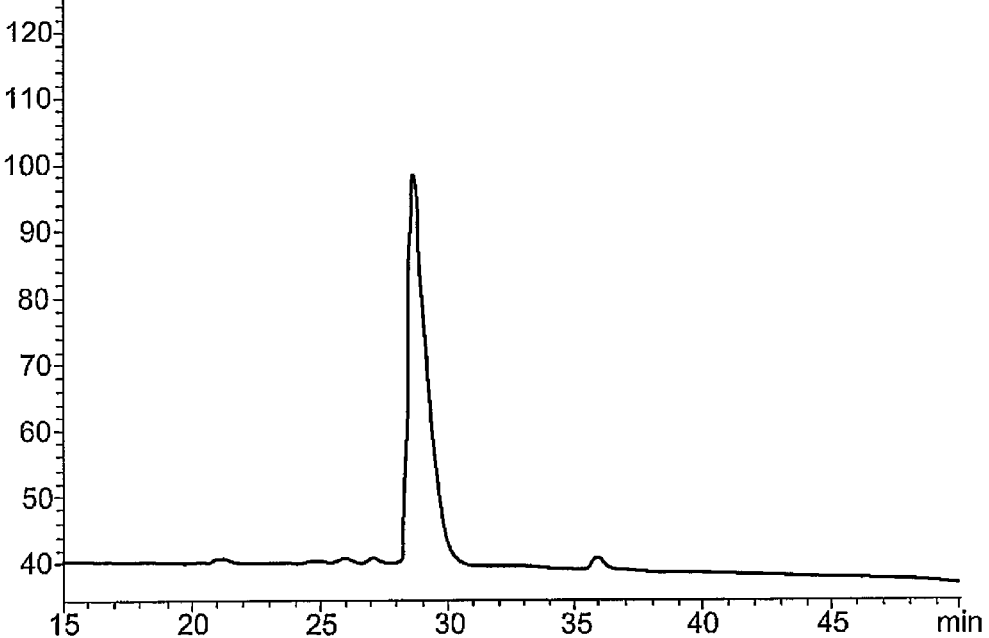
FIG. 13A shows a chromatogram from an RP-HPLC analysis of N77Q substituted IL-15 prior to incubation at 37° C. for one week.
Figure 13B:
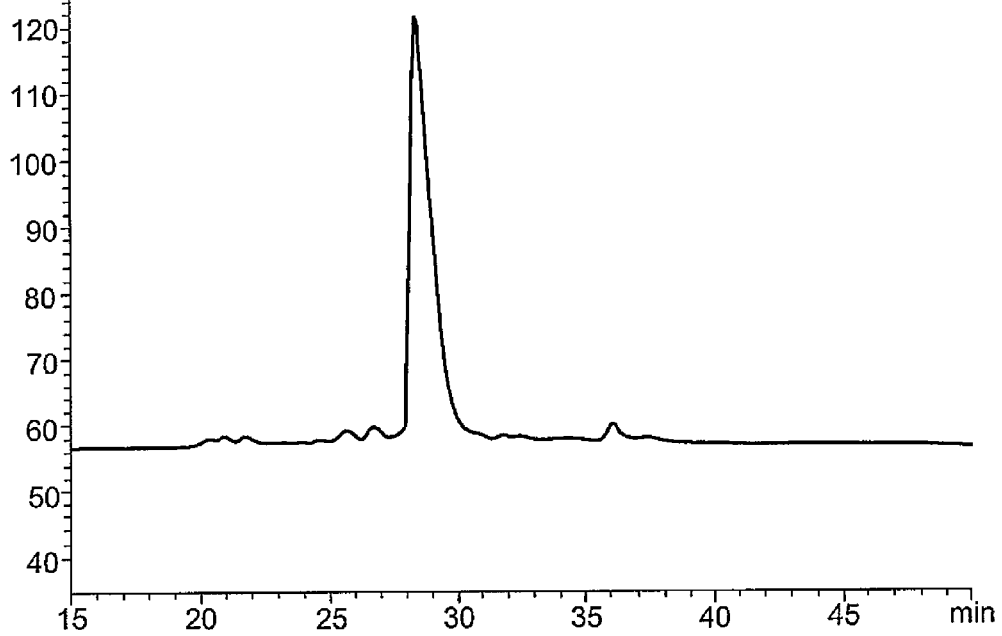
FIG. 13B shows a chromatogram from an RP-HPLC analysis of N77Q substituted IL-15 following incubation at 37° C. for one week.
Figure 14A:
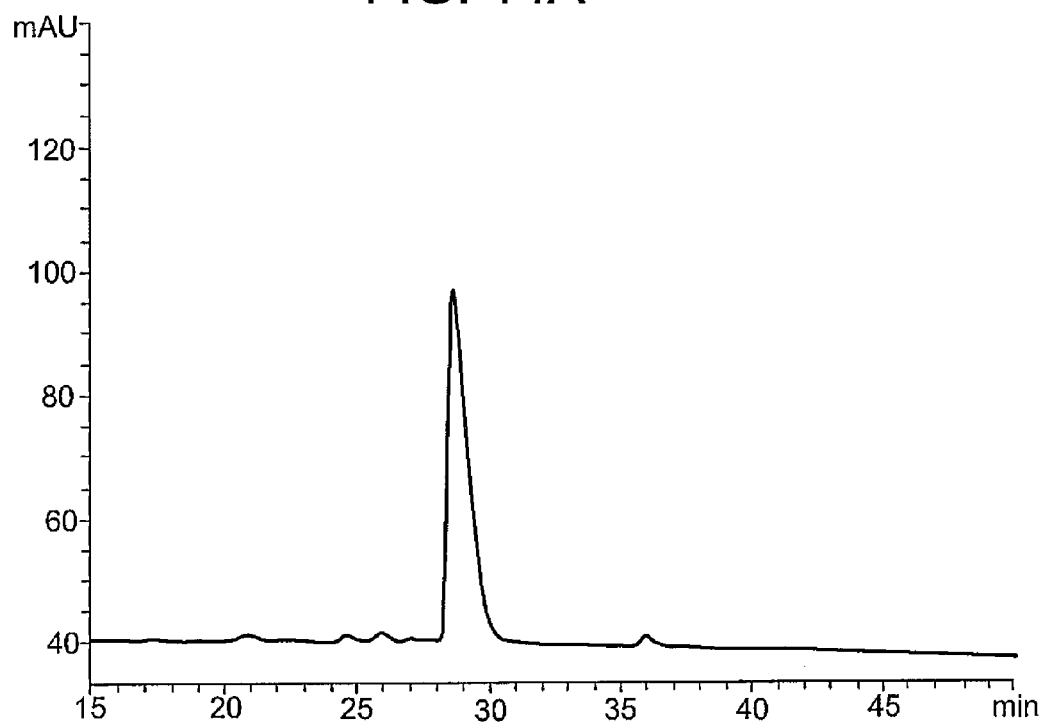
FIG. 14A shows a chromatogram from an RP-HPLC analysis of G78A substituted IL-15 prior to incubation at 37° C. for one week.
Figure 14B:
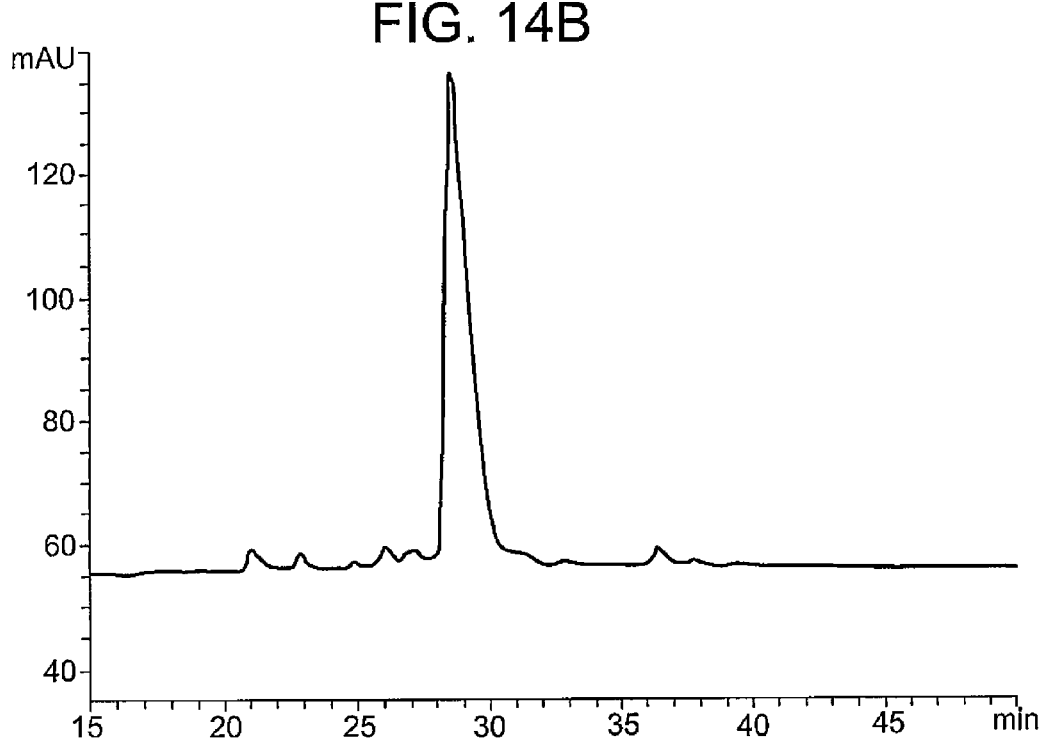
FIG. 14B shows a chromatogram from an RP-HPLC analysis of G78A substituted IL-15 following incubation at 37° C. for one week.

The six IL-15 preparations were simultaneously incubated at 37° C. for one week. At intervals, the percentages of target IL-15 remaining undegraded in each preparation were measured using automated C18 RP-HPLC analysis. The unsubstituted IL-15 preparation degraded rapidly and produced the profile typical of IL-15 deamidation (FIG. 10B). However, the five IL-15 substituted preparations were resistant to degradation (FIGS. 11B, 12B, 13B, 14B, and 15B).

Figure 16:
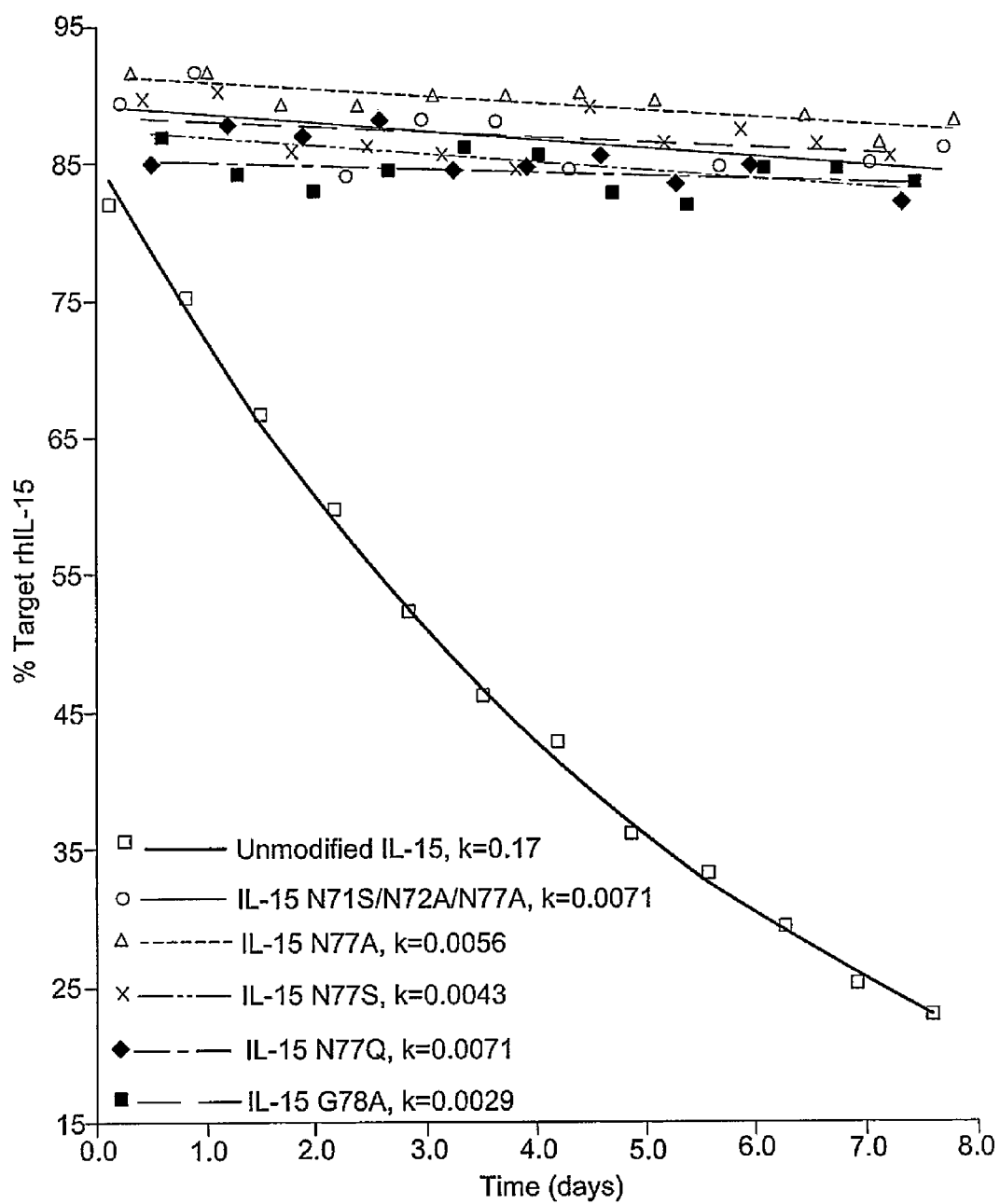
FIG. 16 is a graph showing the degradation rates (as percent target IL-15) of unsubstituted IL-15 (open squares); N71S/N72A/N77A substituted IL-15 (circles); N77A substituted IL-15 (triangles); N77S substituted IL-15 (X); N77Q substituted IL-15 (diamonds); and G78A substituted IL-15 (closed squares) over time (days).

Exponential decay curves were fit to the RP-HPLC data and rate constants were calculated (FIG. 16). The stability of the singly substituted preparations matched that of the triply substituted preparation. As such, although triple-substitution is capable of stabilizing IL-15, triple substitution is not necessary to stabilize IL-15. Any one of the four single-substitutions (N77A, N77S, N77Q, or G78A) was sufficient to decrease the rate of IL-15 degradation more than 20-fold.

This example demonstrated that each of N77A, N77S, N77Q, and G78A single-substituted IL-15 and N71S/N72A/N77A triply-substituted IL-15 decrease the rate of IL-15 degradation more than 20-fold.

Example 9

This example demonstrates that the N77A single-substituted IL-15 and the N71S/N72A/N77A triply-substituted IL-15 have a potency comparable to that of unmodified IL-15.

Unmodified IL-15, N77A single-substituted IL-15, and N71S/N72A/N77A triply-substituted IL-15 were assayed for cell proliferation potency in vitro using a CCTL-2 cell proliferation potency assay. A previously-qualified IL-15 reference (unmodified) preparation was simultaneously assayed to confirm assay performance and to standardize results (100%).

CCTL-2 cells (American Type Culture Collection (ATCC) TIB-214 T-lymphocyte, mouse) were grown under sterile cell culture conditions (37±2° C., 5±2% $CO_2$ and ≧70 humidity) in Lonza RPMI 1640 culture medium containing added L-Glutatmine and 10% heat inactivated fetal bovine serum. Recombinant human IL-2 (200 U/mL) was introduced to the culture medium to enable initial cell line expansion. The cells were harvested, rinsed with an assay medium having no added IL-2, counted for number and viability, distributed into 96-well plates at a density of $5 \times 10^5$ cells/ml (viable cells), and incubated for 4 hours as described above. Test samples were diluted into assay medium and then added to test cells such that the final IL-15 total protein concentrations in the culture wells were between 0.01 and 1 ng/mL. The plates were incubated under standard conditions for 48 hours, followed by addition of sodium dodecyl sulfate and an electron transport indicator reagent (MTS) to produce a colorimetric response proportionate to the number of viable cells. A 96-well plate reader was used to measure the colorimetric response.

Figure 17:
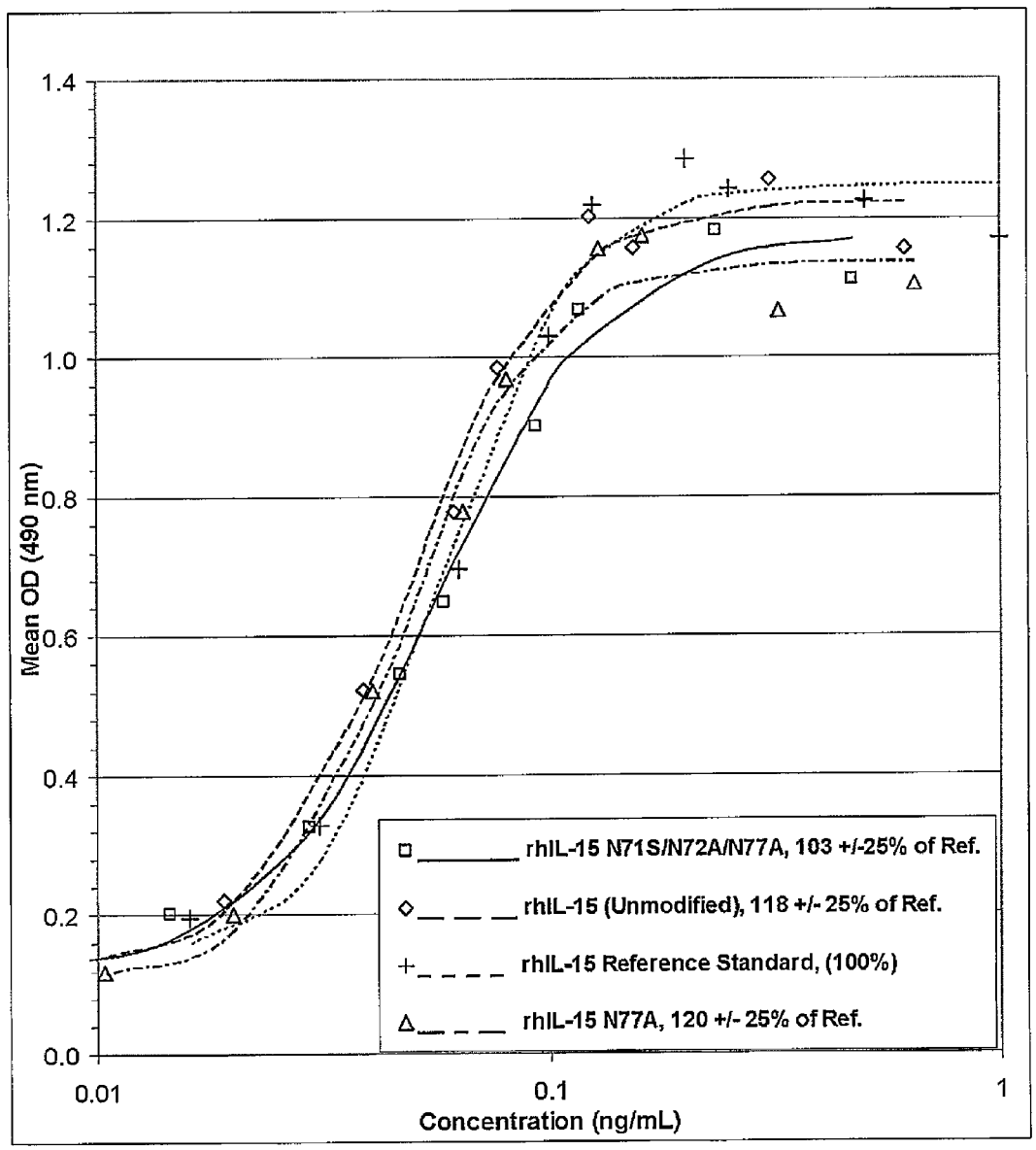
FIG. 17 is a graph showing cell proliferation (as mean optical density (OD) at 490 nm) of unsubstituted IL-15 (diamonds); N71S/N72A/N77A substituted IL-15 (squares); N77A substituted IL-15 (triangles); and reference standard IL-15 (+) over concentration of protein (ng/mL).

The results are shown in FIG. 17. Assay trends for test samples were comparable in terms of initial and final mean optical densities (ODs), transition slopes, and $IC_{50}$ values. Within the assay uncertainty range, the four IL-15 preparations (Reference Standard, Unmodified, N77A, and N71S/N72A/N77A) promoted CCTL-2 cell proliferation with respective $ED_{50}$ values of 0.0590 ng/ml (defined as 100% response); 0.0487 ng/ml, (118±25% of ref.); 0.0478 ng/ml, (120±25% of ref.); and 0.0557 ng/ml, (103±25% of ref.). Therefore, substitution of IL-15 at amino acid N77 alone or at each of N71, N72 and N77 combined maintained IL-15 preparation potency.

This example demonstrated that the N77A single-substituted IL-15 and the N71S/N72A/N77A triply-substituted IL-15 are equivalent in potency to unmodified IL-15.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified polypeptide comprising SEQ ID NO:1 and having interleukin-15 (IL-15) biological activity, wherein
Xaa71 is selected from the group consisting of Ser, Ala and Asn;
Xaa72 is selected from the group consisting of Ser, Ala and Asn;
Xaa77 is selected from the group consisting of Gln, Ser, Lys, Ala, and Glu; and
Xaa78 is selected from the group consisting of Ser, Ala, and Gly.

2. An isolated or purified polypeptide comprising SEQ ID NO:3 and having IL-15 biological activity, wherein
Xaa71 is selected from the group consisting of Ser, Ala and Asn;
Xaa72 is selected from the group consisting of Ser, Ala and Asn;
Xaa77 is selected from the group consisting of Gln, Ser, Lys, Ala, Glu, and Asn; and
Xaa78 is selected from the group consisting of Ser and Ala.

3. The polypeptide according to claim 1, wherein Xaa77 is Gln.

4. The polypeptide according to claim 1, wherein Xaa77 is Ser.

5. The polypeptide according to claim 1, wherein Xaa77 is Ala.

6. The polypeptide according to claim 1, wherein
Xaa71 is Ser,
Xaa72 is Ala, and
Xaa77 is Ala.

7. The polypeptide according to claim 1, wherein Xaa78 is Ala.

8. A pharmaceutical composition comprising the polypeptide according to claim 1, and a pharmaceutically acceptable carrier.

9. The polypeptide according to claim 2, wherein Xaa77 is Gln.

10. The polypeptide according to claim 2, wherein Xaa77 is Ser.

11. The polypeptide according to claim 2, wherein Xaa77 is Ala.

12. The polypeptide according to claim 2, wherein
Xaa71 is Ser,
Xaa72 is Ala, and
Xaa77 is Ala.

13. A pharmaceutical composition comprising the polypeptide according to claim 2, and a pharmaceutically acceptable carrier.

14. The according to claim 2, wherein Xaa78 is Ala.

15. The polypeptide according to claim 1, wherein
Xaa71 is Asn,
Xaa72 is Asn,
Xaa77 is Ala, and
Xaa78 is Gly.

16. A pharmaceutical composition comprising the polypeptide according to claim 15, and a pharmaceutically acceptable carrier.

17. The polypeptide according to claim 2, wherein
Xaa71 is Asn,
Xaa72 is Asn,
Xaa77 is Ala, and
Xaa78 is Ala.

18. A pharmaceutical composition comprising the polypeptide according to claim 17, and a pharmaceutically acceptable carrier.

* * * * *